(12) United States Patent
Hercouet et al.

(10) Patent No.: US 8,403,999 B2
(45) Date of Patent: Mar. 26, 2013

(54) DYEING AND/OR BLEACHING COMPOSITION COMPRISING A POLYCONDENSATE OF ETHYLENE OXIDE AND PROPYLENE OXIDE

(75) Inventors: Leila Hercouet, Neuilly Plaisance (FR); Marie Giafferi, Villemomble (FR); Liliane Gaillard, Paris (FR); Alain Lagrange, Coupvray (FR); Gautier Deconinck, Saint Gratien (FR); Arnaud Hucher, Courbevoie (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/518,492

(22) PCT Filed: Dec. 13, 2010

(86) PCT No.: PCT/EP2010/069505
§ 371 (c)(1),
(2), (4) Date: Aug. 23, 2012

(87) PCT Pub. No.: WO2011/076603
PCT Pub. Date: Jun. 30, 2011

(65) Prior Publication Data
US 2012/0308498 A1    Dec. 6, 2012

Related U.S. Application Data

(60) Provisional application No. 61/298,656, filed on Jan. 27, 2010, provisional application No. 61/298,659, filed on Jan. 27, 2010.

(30) Foreign Application Priority Data

Dec. 22, 2009  (FR) ........................ 09 59401
Dec. 22, 2009  (FR) ........................ 09 59402

(51) Int. Cl.
*A61Q 5/10*         (2006.01)
(52) U.S. Cl. .............. 8/405; 8/406; 8/431; 8/551; 8/552
(58) Field of Classification Search ............. 8/405, 406, 8/431, 551, 552
See application file for complete search history.

(56) References Cited

U.S. PATENT DOCUMENTS

| | | | |
|---|---|---|---|
| 2,528,378 A | 10/1950 | Mannheimer | |
| 2,781,354 A | 2/1957 | Mannheimer | |
| 3,869,454 A | 3/1975 | Lang et al. | |
| 3,955,918 A | 5/1976 | Lang | |
| 4,003,699 A | 1/1977 | Rose et al. | |
| 4,025,301 A | 5/1977 | Lang | |
| RE30,199 E | 1/1980 | Rose et al. | |
| 4,823,985 A | 4/1989 | Grollier et al. | |
| 5,061,289 A | 10/1991 | Clausen et al. | |
| 5,380,340 A | 1/1995 | Neunhoeffer et al. | |
| 5,708,151 A | 1/1998 | Moeckli et al. | |
| 5,766,576 A | 6/1998 | Lowe et al. | |
| 6,099,592 A | 8/2000 | Vidal et al. | |
| 6,099,593 A | 8/2000 | Terranova et al. | |
| 6,338,741 B1 | 1/2002 | Vidal et al. | |
| 6,645,258 B2 | 11/2003 | Vidal et al. | |
| 6,730,789 B1 | 5/2004 | Birault et al. | |
| 7,311,736 B2 | 12/2007 | Burgaud et al. | |
| 7,399,320 B2 | 7/2008 | Burgaud et al. | |
| 2003/0140430 A1* | 7/2003 | Casperson et al. ............. 8/406 |

FOREIGN PATENT DOCUMENTS

| | | |
|---|---|---|
| DE | 2359399 | 6/1975 |
| DE | 3843892 | 6/1990 |
| DE | 4133957 | 4/1993 |
| DE | 19543988 | 5/1997 |
| EP | 0714954 | 6/1996 |
| EP | 0770375 | 5/1997 |
| EP | 1378544 | 1/2004 |
| EP | 1674073 | 6/2006 |
| EP | 1728500 | 12/2006 |
| FR | 2140205 | 1/1973 |
| FR | 2189006 | 1/1974 |
| FR | 2285851 | 4/1976 |
| FR | 2586913 | 3/1987 |
| FR | 2733749 | 11/1996 |
| FR | 2750048 | 12/1997 |
| FR | 2801308 | 5/2001 |
| FR | 2886136 | 12/2006 |
| GB | 1026978 | 4/1966 |
| GB | 1153196 | 5/1969 |
| JP | 2-19576 | 1/1990 |
| JP | 5-163124 | 6/1993 |
| WO | 94/08969 | 4/1994 |
| WO | 94/08970 | 4/1994 |
| WO | 95/01772 | 1/1995 |
| WO | 95/15144 | 6/1995 |
| WO | 96/15765 | 5/1996 |

OTHER PUBLICATIONS

STIC Search Report dated Oct. 15, 2012.*

(Continued)

*Primary Examiner* — Eisa Elhilo
(74) *Attorney, Agent, or Firm* — O'Brien Jones, PLLC

(57) ABSTRACT

Disclosed herein is a device having one or more compartments, for dyeing keratin fibers, wherein a first compartment contains a dye composition free of oxidizing agent, comprising at least one hair dye and at least one polycondensate of ethylene oxide and propylene oxide, and optionally a second compartment contains an oxidizing composition. Also disclosed is an agent for dyeing and/or bleaching keratin fibers, obtained by mixing a composition A comprising at least one alkaline agent with a composition B comprising at least one oxidizing agent, compositions A and/or B comprising at least one fatty substance free of carboxylic acid groups, at least one polycondensate of ethylene oxide and propylene oxide, and a system of nonionic surfactants, with a weighted HLB of greater than or equal to 8, the amount of fatty substance being greater than 20% of the total weight of the dyeing and/or bleaching agent.

19 Claims, No Drawings

OTHER PUBLICATIONS

William M. Meylan and Philip H. Howard, "Atom/Fragment Contribution Method for Estimating Octanol-Water Partition Coefficients," Journal of Pharmaceutical Sciences, vol. 84, No. 1: pp. 83-92, 1995.
Walter Noll, "Chemistry and Technology of Silicones," Academic Press, New York, San Francisco, London, pp. 1-23, 1968.
Charles Todd and Timothy Byers, "Volatile Silicone Fluids for Cosmetic Formulations," Cosmetics and Toiletries, vol. 91, pp. 29-32, Jan. 1976.
English language abstract of EP 0770375, (1997).
English language abstract of EP 1674073, (2006).
English language abstract of EP 1728500, (2006).
English language abstract of FR 2886136, (2006).
English language abstract of JP 2-19576, (1990).
English language abstract of JP 5-163124, (1993).

* cited by examiner

DYEING AND/OR BLEACHING COMPOSITION COMPRISING A POLYCONDENSATE OF ETHYLENE OXIDE AND PROPYLENE OXIDE

The invention relates to a device having one or more compartments, or "kit", for dyeing keratin fibres, and in particular human keratin fibres such as the hair, in which a first compartment contains a dye composition free of oxidizing agent, comprising, in a suitable dyeing medium, at least one hair dye and at least one polycondensate of ethylene oxide and propylene oxide consisting of polyethylene glycol and polypropylene glycol blocks, and optionally a second compartment contains an oxidizing composition.

The present invention also relates to an agent for dyeing and/or bleaching keratin fibres, and in particular human keratin fibres such as the hair, obtained by mixing a composition A comprising at least one alkaline agent with a composition B comprising at least one oxidizing agent, compositions A and/or B comprising at least one fatty substance free of carboxylic acid groups, at least one polycondensate of ethylene oxide and propylene oxide, and a nonionic surfactant system with a weighted HLB of greater than or equal to 8, the amount of fatty substance being greater than 20% by weight relative to the total weight of the dyeing and/or bleaching agent.

It is known practice to dye keratin fibres, and in particular human keratin fibres such as the hair, with dye compositions comprising oxidation dye precursors, in particular ortho- or para-phenylenediamines, ortho- or para-aminophenols, and heterocyclic compounds such as diaminopyrazole derivatives, pyrazolo[1,5-a]-pyrimidine derivatives, pyrimidine derivatives, pyridine derivatives, indole derivatives and indoline derivatives, which are generally known as oxidation bases. Oxidation dye precursors, or oxidation bases, are colourless or weakly coloured compounds, which, when combined with oxidizing products, can give rise to coloured compounds and dyes via a process of oxidative condensation. Permanent colorations are thus obtained.

It is also known that the shades obtained with these oxidation bases may be varied by combining them with couplers or coloration modifiers, the latter being chosen especially from meta-phenylenediamines, meta-aminophenols, meta-hydroxyphenols and certain heterocyclic compounds.

The variety of molecules used as oxidation bases and couplers allows a wide range of colours to be obtained.

The "permanent" coloration obtained by means of these oxidation dyes should moreover satisfy a certain number of requirements. Thus, it should have no toxicological drawbacks, it should be able to produce shades in the desired intensity, and it should show good remanence with respect to external agents such as light, bad weather, washing, permanent waving, perspiration and rubbing.

The dyes should also be able to cover grey hair, and, finally, they should be as unselective as possible, i.e. they should produce the smallest possible coloration differences along the same keratin fibre, which may indeed be differently sensitized (i.e. damaged) between its end and its root.

The second dyeing method, known as direct or semi-permanent dyeing, comprises the application of direct dyes, which are molecules that have affinity for the fibres and dyes even in the absence of oxidizing agent added to the compositions containing them. Given the nature of the molecules employed, they remain rather at the surface of the fibre and penetrate relatively little into the fibre, when compared with the small oxidation dye precursor molecules.

The direct dyes generally employed are chosen from nitrobenzene, anthraquinone, nitropyridine, azo, methine, azomethine, xanthene, acridine, azine and triarylmethane direct dyes. The chemical species used may be nonionic, anionic (acidic dyes) or cationic (basic dyes). The direct dyes may also be natural dyes.

The majority of the direct dyes used show sufficient solubility in aqueous medium, and many dye supports suitable for using them now exist.

These compositions containing one or more direct dyes are applied to the keratin fibres for a time necessary to obtain the desired coloration, and are then rinsed out.

However, the colorations resulting therefrom are particularly chromatic, but temporary or semi-permanent colorations since their desorption from the surface and/or core of the fibre is responsible for their weak dyeing power and poor wash-fastness. These colorations are moreover generally selective.

In the context of dyeing the hair, an oxidizing composition is used to dye hair permanently starting with dye precursors such as oxidation bases and couplers. In the context of direct dyeing, although this method does not require the use of an oxidizing agent to develop the coloration, it is not excluded to use one in order to obtain a lightening effect with the coloration. This is then referred to as direct or semi-permanent dyeing under lightening conditions.

Processes for bleaching keratin fibres consist in employing an aqueous composition comprising at least one oxidizing agent, under alkaline pH conditions in the vast majority of cases. The role of this oxidizing agent is to degrade the melanin of the hair, which, as a function of the nature of the oxidizing agent present, leads to more or less pronounced lightening of the fibres. Thus, for relatively weak lightening, the oxidizing agent is generally hydrogen peroxide. When more substantial lightening is desired, peroxygenated salts are usually used, for instance persulfates, in the presence of hydrogen peroxide.

Many attempts have been made in the field of hair dyeing and/or bleaching in order to improve the properties of dyeing and/or bleaching products using, for example, adjuvants. However, the choice of these adjuvants is difficult insofar as they must improve the dyeing and/or bleaching properties of the compositions without having a detrimental effect on their other properties. In particular, these adjuvants must not be detrimental to the stability of the compositions or their mixing and application properties. If possible, they must limit the olfactory unpleasantness associated with the basifying agents usually used (ammonia or amines).

The results obtained hitherto in the fields both of dyeing and of bleaching are not entirely satisfactory, whether in terms of the resulting colour or in terms of the application qualities.

In the case of dyeing, it is moreover necessary in certain cases, for example when it is desired to improve the uptake of the dyes or to prepare stock solutions of dyes intended to be diluted during the preparation of the shades, to increase the concentration of dyes in the composition.

However, increasing the concentration of dyes is limited by the solubility limit of the dyes in the suitable dyeing medium used for the preparation of the composition, the medium being formed from one or more cosmetically acceptable solvents such as water or alcohols.

The aim of the present invention is to obtain novel compositions for dyeing and/or bleaching keratin fibres, which do not have the drawbacks of the prior art. More particularly, the aim of the present invention is to obtain novel dyeing and/or bleaching compositions that are easy to mix and to apply, that especially do not run and remain well localized at the point of application, and that limit the olfactory problems on application, and also to provide novel compositions for dyeing keratin fibres, which may have a higher concentration of dyes, and especially compositions in which the dyes, although being in an amount greater than their solubility limit in the medium used for the dye composition, are dissolved in this medium, and which are stable over time.

At the same time, the dyeing and/or bleaching composition must be very effective in terms of dyeing and/or bleaching. In particular, as regards dyeing, it must make it possible to obtain powerful, fast, sparingly selective dyeing results that can also give varied shades.

This aim is achieved with the present invention, one subject of which is a multi-compartment device or "kit" for dyeing keratin fibres, and in particular human keratin fibres such as the hair, in which a first compartment contains a dye composition free of oxidizing agent, comprising, in a suitable dyeing medium:
one or more hair dyes; and
one or more polycondensates of ethylene oxide and propylene oxide, consisting of polyethylene glycol and polypropylene glycol blocks having the following chemical structure:

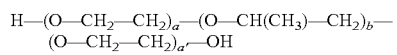

in which formula a and a' range from 2 to 150, and b ranges from 1 to 100;
with the exception of the following composition:

| INCI name | g % |
|---|---|
| Beheneth-10 | 6.00 |
| Sorbitol | 5.00 |
| Liquid petroleum jelly | 60.25 |
| Water | 10.00 |
| Ethanol | 2.00 |
| Poloxamer 184 | 5.00 |
| Potassium bicarbonate | 1.75 |
| Water | 4.302 |
| Monoethanolamine | 5.00 |
| p-Phenylenediamine | 0.216 |
| 2,4-Diaminophenoxyethanol dihydrochloride | 0.482 | and of the following composition obtained by mixing the emulsion A1:

| Emulsion A1 | | |
|---|---|---|
| Phase | INCI name | g % |
| A | Beheneth-10 | 6.00 |
| | Sorbitol | 5.00 |
| | Liquid petroleum jelly | 60.25 |
| | Water | 10.00 |
| B | Ethanol | 2.00 |
| | Poloxamer 184 | 5.00 |
| | Potassium bicarbonate | 1.75 |
| | Water | 4.302 |
| | Monoethanolamine | 5.00 |
| | p-Phenylenediamine | 0.216 |
| | 2,4-Diaminophenoxyethanol dihydrochloride | 0.482 | with an aqueous composition (B) comprising a dispersion of fatty alcohols in water (8%) and 6% hydrogen peroxide in a ratio of 1 part by weight of (A1) per 1.5 parts by weight of (B);
and optionally a second compartment contains an oxidizing composition.

A subject of the present invention is also an agent for dyeing and/or bleaching keratin fibres, and in particular human keratin fibres such as the hair, obtained by mixing a composition A comprising one or more alkaline agents with a composition B comprising one or more oxidizing agents, compositions A and/or B comprising one or more fatty substances free of carboxylic acid groups, one or more polycondensates of ethylene oxide and propylene oxide, and a system of one or more nonionic surfactants other than the polycondensates of ethylene oxide and propylene oxide, with a weighted HLB value of greater than or equal to 8, the amount of fatty substance being greater than 20% by weight relative to the total weight of the dyeing and/or bleaching agent, with the exception of an agent obtained by mixing a composition (A) below:

| Emulsion A1 | | |
|---|---|---|
| Phase | INCI name | g % |
| A | Beheneth-10 | 6.00 |
| | Sorbitol | 5.00 |
| | Liquid petroleum jelly | 60.25 |
| | Water | 10.00 |
| B | Ethanol | 2.00 |
| | Poloxamer 184 | 5.00 |
| | Potassium bicarbonate | 1.75 |
| | Water | 4.302 |
| | Monoethanolamine | 5.00 |
| | p-Phenylenediamine | 0.216 |
| | 2,4-Diaminophenoxyethanol dihydrochloride | 0.482 | and of an aqueous composition (B1) comprising a dispersion of fatty alcohols in water (8%) and 6% of hydrogen peroxide in a ratio of 1 part by weight of (A) per 1.5 parts by weight of (B).

Another subject of the present invention is a dyeing and/or bleaching process using the compositions in accordance with the invention.

Finally, a subject of the present invention is the use of the compositions in accordance with the invention for dyeing and/or bleaching keratin fibres.

The present invention makes it possible to obtain compositions for dyeing and/or bleaching keratin fibres, which are stable over time and whose mixture has a satisfactory consistency for application to the head.

The present invention makes it possible to obtain a composition for dyeing keratin fibres that has a higher concentration of dyes, for example a composition in which the dyes dissolved in the medium are in an amount greater than their solubility limit in that medium, and which is stable over time, for example on storage at 45° C.

In the case of dyeing, the present invention makes it possible to obtain good dyeing properties, especially powerful, chromatic, aesthetic, sparingly selective colorations that show good resistance to the various attacking factors to which the hair may be subjected, such as shampoos, light, sweat and permanent-reshaping operations, while at the same time limiting any olfactory problems.

In the case of bleaching, the present invention makes it possible to obtain a good lightening effect on keratin fibres, while at the same time limiting any olfactory problems.

Unless otherwise indicated, the limits of the ranges of values that are given in the context of the present invention are included in those ranges.

A first subject of the invention is a device having one or more compartments, or "kit", for dyeing keratin fibres, and in particular human keratin fibres such as the hair, in which a first compartment contains a dye composition free of oxidizing agent, comprising, in a suitable dyeing medium, at least one hair dye and at least one polycondensate of ethylene oxide and propylene oxide consisting of polyethylene glycol and polypropylene glycol blocks, and optionally a second compartment contains an oxidizing composition.

For the purposes of the present invention, the term "hair dye" means synthetic direct dyes, natural dyes and oxidation dye precursors.

These hair dyes may be nonionic or ionic, in particular cationic or anionic.

The term "natural dye" means any dye or dye precursor that is naturally occurring and produced either by extraction (and optionally purification) from a plant matrix, or by chemical synthesis.

In contrast, the term "synthetic dye" means any dye that is not naturally occurring.

The oxidation dye precursor(s) present in the composition of the present invention may be chosen from the oxidation bases and couplers conventionally used in oxidation dyeing.

The oxidation base(s) may be chosen from para-phenylenediamines, bis(phenyl)alkylenediamines, para-aminophenols, bis-para-aminophenols, ortho-aminophenols, ortho-phenylenediamines and heterocyclic bases, and the addition salts thereof.

Among the para-phenylenediamines, examples that may be mentioned include para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis($\beta$-hydroxyethyl)-para-phenylenediamine, 4-N,N-bis($\beta$-hydroxyethyl)amino-2-methylaniline, 4-N,N-bis($\beta$-hydroxyethyl)amino-2-chloro-aniline, 2-$\beta$-hydroxyethyl-para-phenylenediamine, 2-fluoro-para-phenylenediamine, 2-isopropyl-para-phenylenediamine, N-($\beta$-hydroxypropyl)-para-phenylenediamine, 2-hydroxymethyl-para-phenylenediamine, N,N-dimethyl-3-methyl-para-phenylenediamine, N-ethyl-N-($\beta$-hydroxy-ethyl)-para-phenylenediamine, N-($\beta$,$\gamma$-dihydroxypropyl)-para-phenylenediamine, N-(4'-aminophenyl)-para-phenylenediamine, N-phenyl-para-phenylenediamine, 2-$\beta$-hydroxyethyloxy-para-phenylenediamine, 2-$\beta$-acetylaminoethyloxy-para-phenylenediamine, N-($\beta$-methoxyethyl)-para-phenylenediamine, 4-aminophenylpyrrolidine, 2-thienyl-para-phenylenediamine, 2-$\beta$-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-$\beta$-hydroxyethyl-para-phenylenediamine, 2-$\beta$-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis($\beta$-hydroxyethyl)-para-phenylenediamine, 2-chloro-para-phenylenediamine and 2-$\beta$-acetylamino-ethyloxy-para-phenylenediamine, and the addition salts thereof with an acid, are particularly preferred.

Among the bis(phenyl)alkylenediamines, examples that may be mentioned include N,N'-bis($\beta$-hydroxyethyl)-N,N'-bis(4'-aminophenyl)-1,3-diaminopropanol, N,N'-bis($\beta$-hydroxyethyl)-N,N'-bis(4'-aminophenyl)ethylenediamine, N,N'-bis(4-aminophenyl)tetramethylenediamine, N,N'-bis($\beta$-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts thereof.

Among the para-aminophenols, examples that may be mentioned include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-($\beta$-hydroxyethylaminomethyl)phenol and 4-amino-2-fluorophenol, and the addition salts thereof with an acid.

Among the ortho-aminophenols, examples that may be mentioned include 2-aminophenol, 2-amino-5-methylphenol, 2-amino-6-methylphenol and 5-acetamido-2-aminophenol, and the addition salts thereof.

Among the heterocyclic bases, examples that may be mentioned include pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-amino-pyridine, 2,3-diamino-6-methoxypyridine, 2-($\beta$-methoxyethyl)amino-3-amino-6-methoxypyridine and 3,4-diaminopyridine, and the addition salts thereof.

Other pyridine oxidation bases that are useful in the present invention are the 3-aminopyrazolo[1,5-a]-pyridine oxidation bases or addition salts thereof described, for example, in patent application FR 2 801 308. Examples that may be mentioned include pyrazolo[1,5-a]pyrid-3-ylamine, 2-acetylaminopyrazolo-[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-yl-amine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo-[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-yl-pyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo [1,5-a]pyrid-5-yl)(2-hydroxyethyl)amino]ethanol, 2-[(3-aminopyrazolo[1,5-a]pyrid-7-yl)(2-hydroxyethyl)amino] ethanol, 3-amino-pyrazolo[1,5-a]pyridin-5-ol, 3-aminopyrazolo[1,5-a]-pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives that may be mentioned are the compounds described, for example, in patents DE 2 359 399; JP 88-169 571; JP 05-63124; EP 0 770 375 or patent application WO 96/15765, for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triamino-pyrimidine, pyrazolopyrimidine derivatives such as those mentioned in patent application FR-A-2 750 048, and among which mention may be made of pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-amino-pyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)-amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolyl-propylaminopyrazolo[1,5-a]pyrimidine, and the addition salts thereof, and the tautomeric forms thereof, when a tautomeric equilibrium exists.

Among the pyrazole derivatives that may be mentioned are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)-pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole and 2,3-diamino-6,7-dihydro-1H,5H-pyrazolo[1,2-a]pyrazol-1-one, and the addition salts thereof. 4,5-Diamino-1-(β-methoxyethyl)-pyrazole may also be used.

A 4,5-diaminopyrazole will preferably be used, and even more preferentially 4,5-diamino-1-(β-hydroxyethyl)pyrazole and/or a salt thereof.

Pyrazole derivatives that may also be mentioned include diamino-N,N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

2,3-Diamino-6,7-dihydro-1H,5H-pyrazolo[1,2-a]-pyrazol-1-one and/or a salt thereof will preferably be used.

Heterocyclic bases that will preferentially be used include 4,5-diamino-1-(β-hydroxyethyl)pyrazole and/or 2,3-diamino-6,7-dihydro-1H,5H-pyrazolo[1,2-a]pyrazol-1-one and/or a salt thereof.

The coupler(s) present in the composition in accordance with the present invention may be chosen from meta-phenylenediamines, meta-aminophenols, meta-diphenols, naphthalene-based couplers and heterocyclic couplers, and the addition salts thereof.

Examples that may be mentioned include 3-aminophenol, 2-methyl-5-aminophenol, 2-methyl-5-(β-hydroxyethylamino)phenol, 2-chloro-6-methyl-3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxy-indole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)-amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

The oxidation base(s) present in the dye composition that is useful in the context of the invention are each generally in an amount of between 0.001% and 10% by weight and preferably between 0.005% and 6% by weight approximately relative to the total weight of the dye composition.

The coupler(s) present in the dye composition that is useful in the context of the invention are each generally in an amount of between 0.001% and 10% by weight and preferably between 0.005% and 6% by weight approximately relative to the total weight of the dye composition.

In general, the addition salts of the oxidation bases and couplers that may be used in the context of the invention are especially chosen from the addition salts with an acid such as the hydrochlorides, hydrobromides, sulfates, citrates, succinates, tartrates, lactates, $(C_1-C_4)$alkylsulfonates, and in particular methanesulfonates, tosylates, benzene-sulfonates, phosphates and acetates, and the addition salts with a base such as sodium hydroxide, potassium hydroxide, ammonia, amines or alkanolamines.

As examples of synthetic direct dyes that are suitable for use, mention may be made of azo direct dyes, methine direct dyes, carbonyl direct dyes, azine direct dyes, nitro(hetero)aryl direct dyes, especially nitrobenzene dyes, and tri(hetero)arylmethane direct dyes, and the addition salts thereof; alone or as mixtures.

More particularly, the azo dyes comprise an —N═N— function in which the two nitrogen atoms are not simultaneously engaged in a ring. However, it is not excluded for one of the two nitrogen atoms of the sequence —N═N— to be engaged in a ring.

The dyes of the methine family are more particularly compounds comprising at least one sequence selected from >C═C< and —N═C< in which the two atoms are not simultaneously engaged in a ring. However, it is pointed out that one of the nitrogen or carbon atoms of the sequences may be engaged in a ring. More particularly, the dyes of this family are derived from compounds of true methine type (comprising one or more abovementioned sequences —C═C—); of azomethine type (comprising at least one, or more, sequences —C═N—) with, for example, azacarbocyanins and their isomers, diazacarbocyanins and their isomers, and tetraazacarbocyanins; of mono- and diarylmethane type; of indoamine (or diphenylamine) type; of indophenol type; or of indoaniline type.

As regards the dyes of the carbonyl family, examples that may be mentioned include dyes chosen from acridone, benzoquinone, anthraquinone, naphthoquinone, benzanthrone, anthranthrone, pyranthrone, pyrazol-anthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole and coumarin dyes.

As regards the dyes of the azine family, mention may be made especially of azine, xanthene, thioxanthene, fluorindine, acridine, (di)oxazine, (di)thiazine and pyronin dyes.

The nitro(hetero)aromatic dyes are more particularly nitrobenzene or nitropyridine direct dyes.

As regards the dyes of porphyrin or phthalocyanin type, it is possible to use cationic or non-cationic compounds, optionally comprising one or more metals or metal ions, for instance alkali metals, alkaline-earth metals, zinc and silicon.

Examples of particularly suitable synthetic direct dyes that may be mentioned include nitrobenzene dyes; azo direct dyes; methine direct dyes; azomethine direct dyes, with, more particularly, diazacarbocyanins and isomers thereof and tetraazacarbocyanins (tetraazapentamethines); quinone direct dyes, and in particular anthraquinone, naphthoquinone or benzoquinone dyes; azine direct dyes; xanthene direct dyes; triarylmethane direct dyes; indoamine direct dyes; indigoid direct dyes; phthalocyanin and porphyrin direct dyes; alone or as mixtures.

The direct dyes are preferably selected from nitrobenzene dyes; azo dyes; azomethine dyes, with diazacarbocyanins and isomers thereof, and tetraaza-carbocyanins (tetraazapentamethines); anthraquinone direct dyes; triarylmethane direct dyes; alone or as mixtures.

More preferably still, these direct dyes are selected from nitrobenzene dyes; azo direct dyes; azomethine direct dyes, with diazacarbocyanins and isomers thereof, and tetraazacarbocyanins (tetraazapentamethines); alone or as a mixture.

Among the nitrobenzene direct dyes that may be used according to the invention, mention may be made in a non-limiting manner of the following compounds:

1,4-diamino-2-nitrobenzene;
1-amino-2-nitro-4-β-hydroxyethylaminobenzene;
1-amino-2-nitro-4-bis(β-hydroxyethyl)aminobenzene;
1,4-bis(β-hydroxyethylamino)-2-nitrobenzene;
1-β-hydroxyethylamino-2-nitro-4-bis(β-hydroxyethylamino)benzene;
1-β-hydroxyethylamino-2-nitro-4-aminobenzene;
1-hydroxyethylamino-2-nitro-4-(ethyl)(β-hydroxyethyl)aminobenzene;
1-amino-3-methyl-4-β-hydroxyethylamino-6-nitrobenzene;
1-amino-2-nitro-4-β-hydroxyethylamino-5-chlorobenzene;
1,2-diamino-4-nitrobenzene;
1-amino-2-β-hydroxyethylamino-5-nitrobenzene;
1,2-bis(β-hydroxyethylamino)-4-nitrobenzene;
1-amino-2-tris(hydroxymethyl)methylamino-5-nitrobenzene;
1-hydroxy-2-amino-5-nitrobenzene;
1-hydroxy-2-amino-4-nitrobenzene;
1-hydroxy-3-nitro-4-aminobenzene;
1-hydroxy-2-amino-4,6-dinitrobenzene;
1-β-hydroxyethyloxy-2-β-hydroxyethylamino-5-nitrobenzene;
1-methoxy-2-β-hydroxyethylamino-5-nitrobenzene;
1-β-hydroxyethyloxy-3-methylamino-4-nitrobenzene;
1-β,γ-dihydroxypropyloxy-3-methylamino-4-nitrobenzene;
1-β-hydroxyethylamino-4-β,γ-dihydroxypropyloxy-2-nitrobenzene;
1-β,γ-dihydroxypropylamino-4-trifluoromethyl-2-nitrobenzene;
1-β-hydroxyethylamino-4-trifluoromethyl-2-nitrobenzene;
1-β-hydroxyethylamino-3-methyl-2-nitrobenzene;
1-β-aminoethylamino-5-methoxy-2-nitrobenzene;
1-hydroxy-2-chloro-6-ethylamino-4-nitrobenzene;
1-hydroxy-2-chloro-6-amino-4-nitrobenzene;
1-hydroxy-6-bis(β-hydroxyethyl)amino-3-nitrobenzene;
1-β-hydroxyethylamino-2-nitrobenzene;
1-hydroxy-4-β-hydroxyethylamino-3-nitrobenzene.

Among the azo, azomethine, and methine direct dyes that may be used according to the invention, mention may be made of the cationic dyes described in patent applications WO 95/15144, WO 95/01772 and EP 714 954; FR 2 189 006, FR 2 285 851, FR 2 140 205, EP 1 378 544 and EP 1 674 073.

For example, the synthetic direct dye(s) may be chosen from monochromophoric cationic direct dyes of the following types: azos; methines; azomethines with diazacarbocyanins and isomers thereof, and tetraazacarbocyanins; anthraquinones; alone or as a mixture.

Hence, mention may be made especially of the cationic direct dyes corresponding to the following formulae:

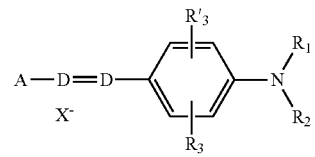

in which:

D represents a nitrogen atom or the —CH group, $R_1$ and $R_2$, which may be identical or different, represent a hydrogen atom; a $C_1$-$C_4$ alkyl radical which may be substituted with a —CN, —OH or —NH$_2$ radical, or form, with a carbon atom of the benzene ring, an optionally oxygenous or nitrogenous heterocycle that may be substituted with one or more $C_1$-$C_4$ alkyl radicals; a 4'-aminophenyl radical, $R_3$ and $R'_3$, which are identical or different, represent a hydrogen or halogen atom selected from chlorine, bromine, iodine and fluorine, or a cyano, $C_1$-$C_4$ alkyl, $C_1$-$C_4$ alkoxy or acetyloxy radical, $X^-$ represents an anion preferably selected from chloride, methyl sulfate and acetate, A represents a group selected from the following structures:

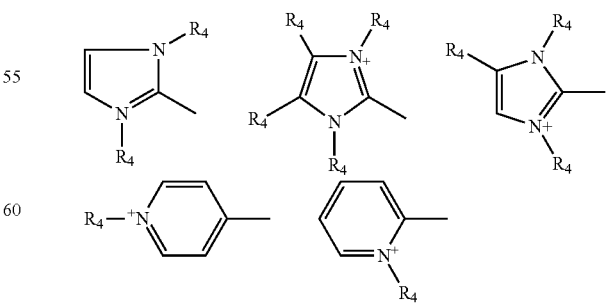

in which $R_4$ represents a $C_1$-$C_4$ alkyl radical that may be substituted with a hydroxyl radical;

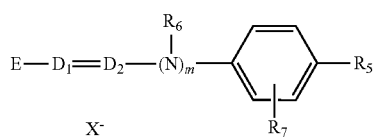

in which:

$R_5$ represents a hydrogen atom, a $C_1$-$C_4$ alkoxy radical or a halogen atom such as bromine, chlorine, iodine or fluorine, $R_6$ represents a hydrogen atom or a $C_1$-$C_4$ alkyl radical or forms, with a carbon atom of the benzene ring, a heterocycle that is optionally oxygenous and/or substituted with one or more $C_1$-$C_4$ alkyl groups, $R_7$ represents a hydrogen or halogen atom such as bromine, chlorine, iodine or fluorine, $D_1$ and $D_2$, which may be identical or different, represent a nitrogen atom or the —CH group, m=0 or 1, X⁻ represents a cosmetically acceptable anion that is preferably selected from chloride, methyl sulfate and acetate, E represents a group selected from the following structures:

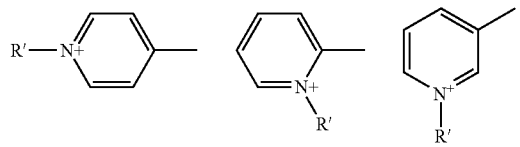

in which R' represents a $C_1$-$C_4$ alkyl radical;

when m=0 and when $D_1$ represents a nitrogen atom, E may then also denote a group of the following structure:

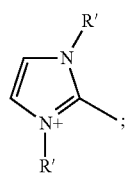

in which R' represents a $C_1$-$C_4$ alkyl radical.

Among the abovementioned compounds, use is made most particularly of the following compounds:

(A1)
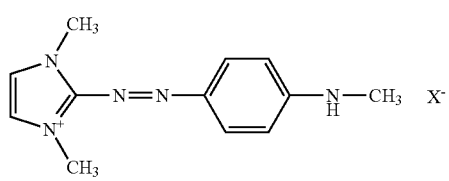

(A2)
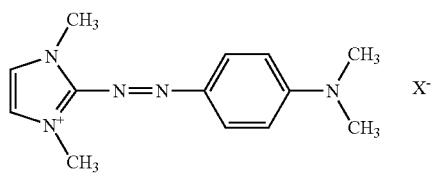

(A3)
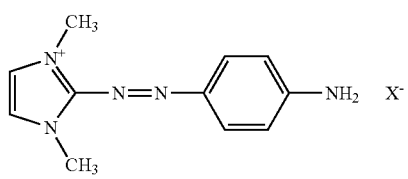

(A4)
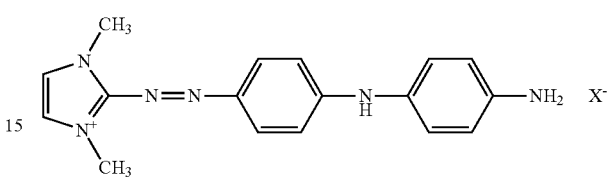

(A5)
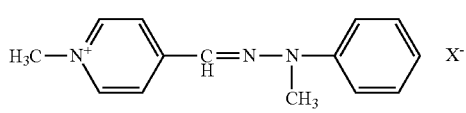

(A6)
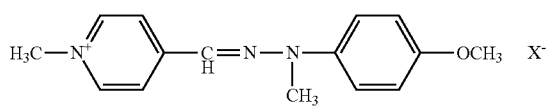

X⁻ representing a cosmetically acceptable anion or mixture of anions.

Among the tetraazapentamethine dyes that may be used according to the invention, mention may be made of the following compounds given in the table below:

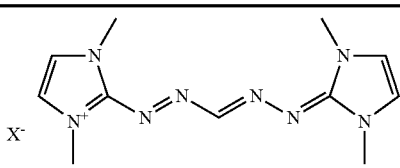

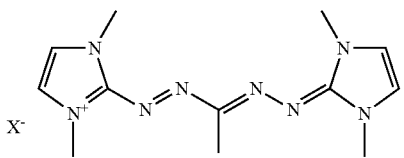

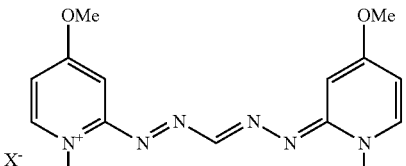

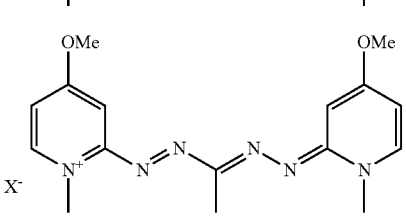

-continued

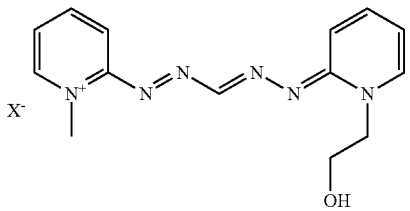

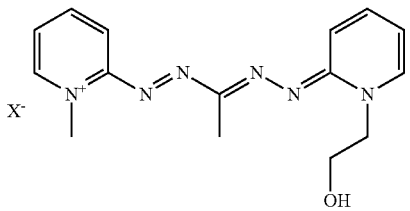

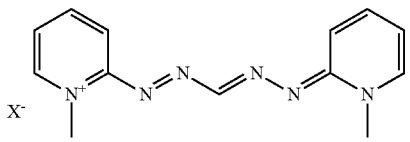

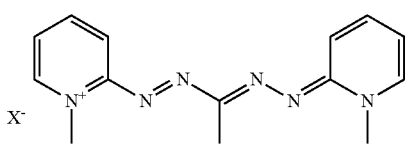

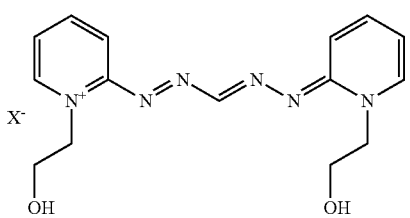

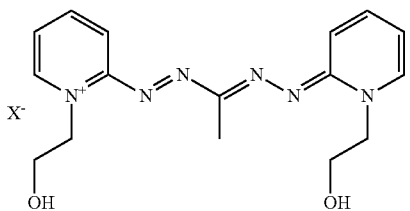

X⁻ represents a cosmetically acceptable anion or mixture of anions, preferably selected from chloride, iodide, methyl sulfate, ethyl sulfate and acetate.

As other dyes that may be used according to the invention, mention may also be made, among the azo direct dyes, of the following dyes, which are described in the Colour Index International, 3rd edition:
Disperse Red 17;
Disperse Red 13;
Basic Red 22;
Basic Red 76;
Basic Yellow 57;
Basic Brown 16;
Basic Brown 17;
Disperse Green 9;
Disperse Black 9;
Solvent Black 3;
Disperse Blue 148;
Disperse Violet 63;
Solvent Orange 7.

Mention may also be made of 1-(4'-aminodiphenylazo)-2-methyl-4-bis(β-hydroxyethyl)amino-benzene (INCI name: HC Yellow 7).

Among the quinone direct dyes that may be mentioned are the following dyes:
Disperse Red 15;
Solvent Violet 13;
Solvent Blue 14;
Disperse Violet 1;
Disperse Violet 4;
Disperse Blue 1;
Disperse Violet 8;
Disperse Blue 3;
Disperse Red 11;
Disperse Blue 7;
Disperse Blue 14;
Basic Blue 22;
Disperse Violet 15;
Disperse Blue 377;
Disperse Blue 60;
Basic Blue 99;
and also the following compounds:
1-N-methylmorpholiniumpropylamino-4-hydroxyanthraquinone;
1-aminopropylamino-4-methylaminoanthraquinone;
1-aminopropylaminoanthraquinone;
5-β-hydroxyethyl-1,4-diaminoanthraquinone;
2-aminoethylaminoanthraquinone;
1,4-bis(βγ-dihydroxypropylamino)anthraquinone.

Mention may also be made of the coumarin compound Disperse Yellow 82.

Among the azine dyes that may be mentioned are the following compounds:
Basic Blue 17;
Basic Red 2;
Solvent Orange 15.

Among the triarylmethane dyes that may be used according to the invention, mention may be made of the following compounds:
Basic Green 1;
Basic Violet 3;
Basic Violet 14;
Basic Blue 7;
Basic Blue 26.

Among the indoamine dyes that may be used according to the invention, mention may be made of the following compounds:
2-β-hydroxyethylamino-5-[bis(β-4'-hydroxyethyl)amino]anilino-1,4-benzoquinone;
2-β-hydroxyethylamino-5-(2'-methoxy-4'-amino)anilino-1,4-benzoquinone;
3-N(2'-chloro-4'-hydroxy)phenylacetylamino-6-methoxy-1,4-benzoquinone imine;
3-N(3'-chloro-4'-methylamino)phenylureido-6-methyl-1,4-benzoquinone imine;
3-[4'-N-(ethylcarbamylmethyl)amino]phenylureido-6-methyl-1,4-benzoquinone imine.

The cationic direct dyes are preferably selected from direct dyes of the following types: azos, methines; azomethines, with diazacarbocyanins and isomers thereof, and tetraazacarbocyanins (tetraazapentamethines); anthraquinones; alone or as a mixture.

For the nonionic dyes, compounds with a log P of greater than or equal to 2 are most particularly preferred.

As regards the synthetic direct dyes with a log P of greater than or equal to 2, it is recalled that the log P value conventionally represents the partition coefficient of the dye between octanol and water. The log P may be calculated according to the method described in the article by Meylan and Howard: *Atom/Fragment contribution method for estimating octanol-water partition coefficients*, J. Pharm. Sci., 84: 83-92, 1995. This value may also be calculated using numerous commercially available software packages, which determine the log P as a function of the structure of a molecule. By way of example, mention may be made of the Epiwin software from the United States Environmental Agency.

In particular, the dyes that are suitable for use in the invention are chosen from the following compounds, alone or as a mixture:

| Dye | Chemical structure | logP |
| --- | --- | --- |
| Disperse Red 17 | 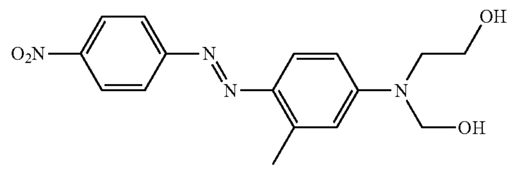 [SMILES: Cc1cc(N(CO)CCO)ccc1/N=N/c1ccc([N+](=O)[O-])cc1] | 3.69 |
| Disperse Violet 1 | 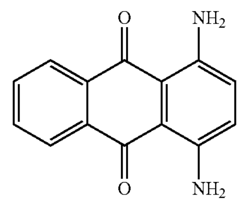 [SMILES: Nc1ccc(N)c2c1C(=O)c1ccccc1C2=O] | 3.0 |
| HC Yellow 7 | 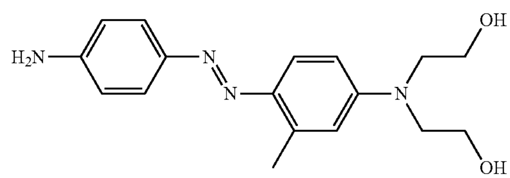 [SMILES: Cc1cc(N(CCO)CCO)ccc1/N=N/c1ccc(N)cc1] | 2.38 |
| Disperse Blue 377 | 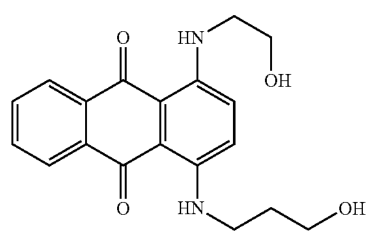 [SMILES: O=C1c2ccccc2C(=O)c2c(NCCCO)ccc(NCCO)c21] | 3.21 |
| Disperse Red 13 | 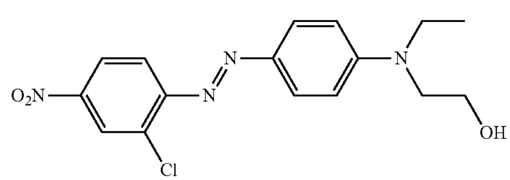 [SMILES: CCN(CCO)c1ccc(/N=N/c2ccc([N+](=O)[O-])cc2Cl)cc1] | 5.22 |
| Disperse Green 9 | 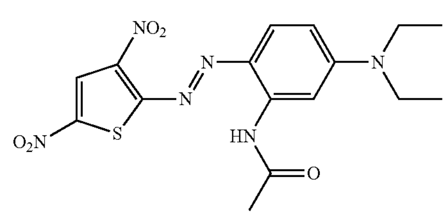 [SMILES: CCN(CC)c1ccc(/N=N/c2sc([N+](=O)[O-])cc2[N+](=O)[O-])c(NC(C)=O)c1] | 4.23 |

-continued

| Dye | Chemical structure | logP |
|---|---|---|
| Solvent Black 3 | 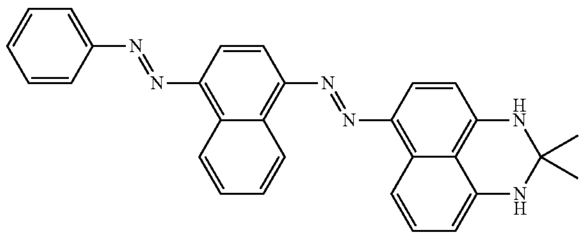 [SMILES: CC1(C)Nc2cccc3c(/N=N/c4ccc(/N=N/c5ccccc5)c5ccccc45)ccc(c23)N1] | 7.50 |
| Disperse Blue 148 | 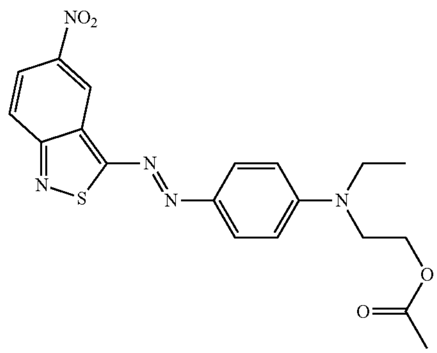 [SMILES: CCN(CCOC(C)=O)c1ccc(/N=N/c2snc3ccc([N+](=O)[O-])cc23)cc1] | 4.81 |
| Disperse Violet 63 | 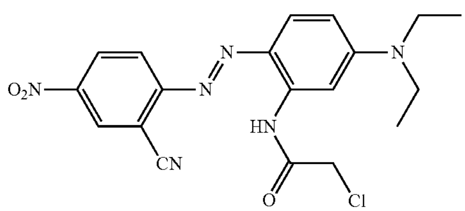 [SMILES: CCN(CC)c1ccc(/N=N/c2ccc([N+](=O)[O-])cc2C#N)c(NC(=O)CCl)c1] | 5.30 |
| Disperse Blue 60 | 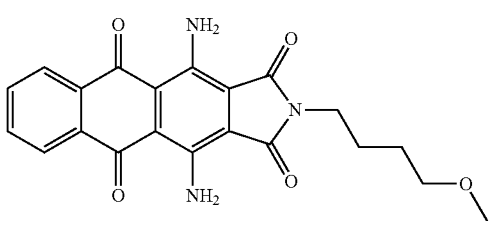 [SMILES: COCCCCn1c(=O)c2c(N)c3c(=O)c4ccccc4c(=O)c3c(N)c2c1=O] | 3.38 |
| Disperse Blue 14 | 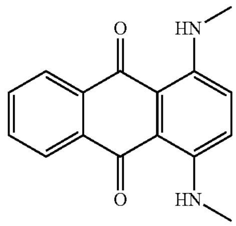 [SMILES: CNc1ccc(NC)c2c1C(=O)c1ccccc1C2=O] | 4.25 |
| Solvent Orange 15 | 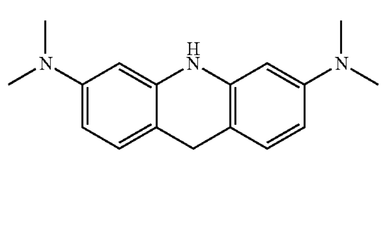 | 3.90 |

| Dye | Chemical structure | logP |
|---|---|---|
| Solvent Orange 7 | 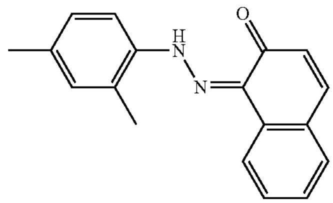 [SMILES: Cc1ccc(N/N=C2\C(=O)C=Cc3ccccc32)c(C)c1] | 4.40 |
| Solvent Blue 14 | 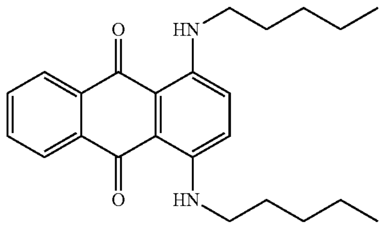 [SMILES: CCCCCNc1ccc(NCCCCC)c2c1C(=O)c1ccccc1C2=O] | 8.18 |
| Disperse Yellow 82 | 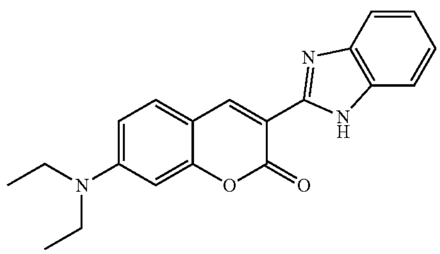 [SMILES: CCN(CC)c1ccc2cc(-c3nc4ccccc4[nH]3)c(=O)oc2c1] | 3.68 |

Even more preferentially, the direct dyes of the invention are chosen from cationic dyes of the following types: azos; methines; azomethines, with diazacarbocyanins and isomers thereof, and tetraazacarbocyanins (tetraazapentamethines); anthraquinones; alone or as a mixture, and in particular dyes (A1) to (A6) mentioned previously, and also nonionic dyes with a log P of greater than or equal to 2.

Among the anionic direct dyes, mention may be made in particular of those described in the Colour Index International 3rd edition under the name Acid, and in particular:
Disperse Red 17
Acid Yellow 9
Acid Black 1
Acid Yellow 36
Acid Orange 7
Acid Red 33
Acid Red 35
Acid Yellow 23
Acid Orange 24
Acid Violet 43
Acid Blue 62
Acid Blue 9
Acid Violet 49
Acid Blue 7.

The synthetic direct dye(s), when they are present, preferably represent from 0.0001% to 10% by weight relative to the weight of the composition, and preferably from 0.005% to 5% by weight relative to the same reference.

The composition according to the invention may comprise one or more natural dyes.

The natural dye(s) that are in particular suitable for use in the invention are preferably chosen from lawsone, juglone, alizarin, purpurin, carminic acid, kermesic acid, laccaic acid, purpurogallin, anthragallol, protocatechaldehyde, indigo, isatin, curcumin, spinulosin, chlorophylls, chlorophyllines, orceins, haematin, haematoxylin, brazilin, brazileine, safflower dyes (for instance carthamine), flavonoids (with, for example, morin, apigenidin and sandalwood), anthocyans (of the apigenidin type), carotenoids, tannins, sorghum and cochineal carmine, or mixtures thereof.

Extracts or decoctions containing these natural dyes, and especially henna-based extracts, may also be used.

Preferably, the natural dye(s) are chosen from lawsone, juglone, alizarin, purpurin, carminic acid, kermesic acid, laccaic acid, purpurogallin, protocatechaldehyde, indigo, isatin, curcumin, spinulosin, apigenidin, chlorophylline, sorghum, orceins, cochineal carmine, haematin, haematoxylin, brazilin and brazileine, and mixtures thereof.

These dyes may optionally be used in the presence of mordants (for example zinc, manganese, aluminium, iron, etc. salts).

The natural dyes, when they are present, preferably represent from 0.001% to 10% by weight, preferably from 0.01% to 8% by weight and better still from 0.1% to 5% by weight relative to the weight of the composition.

Preferably, the dye composition that is useful in the context of the invention comprises one or more oxidation dye precursors.

The polycondensate(s) of ethylene oxide and propylene oxide, consisting of polyethylene glycol and polypropylene glycol blocks, present in the dye composition that is useful in the context of the invention are polyethylene glycol/polypropylene glycol/polyethylene glycol triblock copolymers having the following chemical structure:

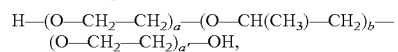

in which formula a and a' range from 2 to 150, and b ranges from 1 to 100.

Preferably, a and a' range from 10 to 130 and b ranges from 20 to 80. Preferably, a and a' are identical.

According to one particular embodiment of the invention, the polycondensate(s) of ethylene oxide and propylene oxide have a weight-average molecular weight ranging from 1000 to 15 000, better still ranging from 1500 to 15 000, in particular ranging from 1500 to 10 000 and even better still ranging from 1500 to 5000.

Advantageously, the polycondensate(s) of ethylene oxide and propylene oxide have a cloud point, at 10 g/l in distilled water, of greater than or equal to 20° C. and preferably greater than or equal to 60° C. The cloud point is measured according to standard ISO 1065.

As polycondensates of ethylene oxide and propylene oxide that may be used according to the invention, mention may be made of the polyethylene glycol/polypropylene glycol/polyethylene glycol triblock polycondensates sold under the name Synperonic, for instance Synperonic® PE/F32 (INCI name: Poloxamer 108), Synperonic® PE/F108 (INCI name: Poloxamer 338), Synperonic® PE/L44 (INCI name: Poloxamer 124), Synperonic® PE/L42 (INCI name: Poloxamer 122), Synperonic® PE/F127 (INCI name: Poloxamer 407), Synperonic® PE/F88 (INCI name: Poloxamer 238), Synperonic® PE/L64 (INCI name: Poloxamer 184) by the company Croda, or Lutrol® F68 (INCI name: Poloxamer 188) by the company BASF.

The polycondensate(s) of ethylene oxide and propylene oxide may be present in the dye composition that is useful in the context of the invention in a content at least equal to 1% by weight, preferably ranging from 1% to 50%, preferably from 5% to 40% and better still from 10% to 30% by weight relative to the total weight of the composition.

According to one particular embodiment, the dye composition that is useful in the context of the present invention comprises one or more fatty substances free of carboxylic acid groups.

The term "fatty substances" means organic compounds that are insoluble in water at ordinary temperature (25° C.) and at atmospheric pressure (760 mmHg) (solubility of less than 5%, preferably 1% and even more preferentially 0.1%). They have in their structure a sequence of at least two siloxane groups or at least one hydrocarbon-based chain comprising at least 6 carbon atoms. In addition, the fatty substances are generally soluble in organic solvents under the same temperature and pressure conditions, for instance chloroform, ethanol, benzene or decamethylcyclopentasiloxane.

The fatty substances are especially chosen from lower alkanes, fatty alcohols, fatty acid esters, fatty alcohol esters, oils, in particular mineral, plant, animal or synthetic non-silicone oils, non-silicone waxes, and silicones.

It is recalled that, for the purposes of the invention, the fatty alcohols, fatty esters and fatty acids more particularly contain one or more linear or branched, saturated or unsaturated hydrocarbon-based groups comprising 6 to 30 carbon atoms, which is (are) optionally substituted, in particular with one or more hydroxyl groups (in particular 1 to 4). If they are unsaturated, these compounds may comprise one to three conjugated or unconjugated carbon-carbon double bonds.

As regards lower alkanes, these alkanes comprise from 6 to 16 carbon atoms and are linear or branched, optionally cyclic. By way of example, the alkanes may be chosen from hexane and dodecane, isoparaffins such as isohexadecane and isodecane.

As non-silicone oils that may be used in the composition of the invention, examples that may be mentioned include:
hydrocarbon-based oils of animal origin, such as perhydrosqualene;
hydrocarbon-based oils of plant origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesameseed oil, hazelnut oil, apricot oil, macadamia oil, arara oil, castor oil, avocado oil, caprylic/capric acid triglycerides, for instance those sold by the company Stearineries Dubois or those sold under the names Miglyol® 810, 812 and 818 by the company Dynamit Nobel, jojoba oil and Shea butter oil;
linear or branched hydrocarbons of more than 16 carbon atoms and of mineral or synthetic origin, such as liquid paraffins, petroleum jelly, liquid petroleum jelly, polydecenes, and hydrogenated polyisobutenes such as Parleam®;
fluoro oils, for instance perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that may be used in the composition of the invention are not oxyalkylenated. They are saturated or unsaturated, linear or branched and comprise from 6 to 30 carbon atoms and more particularly from 8 to 30 carbon atoms. Mention may be made of cetyl alcohol, stearyl alcohol and the mixture thereof (cetylstearyl alcohol), octyldodecanol, 2-butyloctanol, 2-hexyldecanol, 2-undecylpentadecanol, oleyl alcohol or linoleyl alcohol.

The non-silicone wax(es) that may be used in the composition of the invention are chosen from carnauba wax, candelilla wax, esparto grass wax, paraffin wax, ozokerites, plant waxes such as olive wax, rice wax, hydrogenated jojoba wax or the absolute waxes of flowers such as the essential wax of blackcurrant blossom sold by the company Bertin (France), animal waxes, for instance beeswaxes or modified beeswaxes (cerabellina); other waxes or waxy starting materials that may be used according to the invention are especially marine waxes such as the product sold by the company Sophim under the reference M82, and polyethylene waxes or polyolefin waxes in general.

The esters are esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters being more particularly greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isonnonate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still in the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

The following may especially be mentioned: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition may also comprise, as fatty ester, sugar esters and diesters of $C_6$-$C_{30}$ and preferably $C_{12}$-$C_{22}$ fatty acids. It is recalled that the term "sugar" means oxygenous hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from mono-, di-, tri-, tetraesters and polyesters, and mixtures thereof.

These esters may be chosen, for example, from oleates, laurates, palmitates, myristates, behenates, cocoates, stearates, linoleates, linolenates, caprates and arachidonates, or mixtures thereof such as, especially, oleo-palmitate, oleo-stearate and palmitostearate mixed esters.

It is more particularly preferred to use monoesters and diesters and especially sucrose, glucose or methylglucose mono- or dioleates, stearates, behenates, oleopalmitates, linoleates, linolenates and oleostearates.

An example that may be mentioned is the product sold under the name Glucate® DO by the company Amerchol, which is a methylglucose dioleate.

Examples of esters or mixtures of esters of sugar and of fatty acid that may also be mentioned include:
the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
the products sold under the name Ryoto Sugar Esters, for example referenced B370 and corresponding to sucrose behenate formed from 20% monoester and 80% di-tri-ester-polyester;
the sucrose mono-dipalmito-stearate sold by the company Goldschmidt under the name Tegosoft® PSE.

The silicones that may be used in the composition of the present invention are volatile or non-volatile, cyclic, linear or branched silicones, which are unmodified or modified with organic groups, having a viscosity from $5 \times 10^{-6}$ to 2.5 m²/s at 25° C., and preferably $1 \times 10^{-5}$ to 1 m²/s.

The silicones that may be used in accordance with the invention may be in the form of oils, waxes, resins or gums.

Preferably, the silicone is chosen from polydialkylsiloxanes, especially polydimethylsiloxanes (PDMS), and organomodified polysiloxanes comprising at least one functional group chosen from poly(oxy-alkylene) groups, amino groups and alkoxy groups.

The organopolysiloxanes are defined in greater detail in Walter Noll's *Chemistry and Technology of Silicones* (1968), Academic Press. They may be volatile or non-volatile.

When they are volatile, the silicones are more particularly chosen from those having a boiling point of between 60° C. and 260° C., and even more particularly from:

(i) cyclic polydialkylsiloxanes comprising from 3 to 7 and preferably 4 to 5 silicon atoms. These are, for example, octamethylcyclotetrasiloxane sold in particular under the name Volatile Silicone® 7207 by Union Carbide or Silbione® 70045 V 2 by Rhodia, decamethylcyclopentasiloxane sold under the name Volatile Silicone® 7158 by Union Carbide, and Silbione® 70045 V 5 by Rhodia, and mixtures thereof.

Mention may also be made of cyclocopolymers of the dimethylsiloxane/methylalkylsiloxane type, such as Volatile Silicone® FZ 3109 sold by the company Union Carbide, of formula:

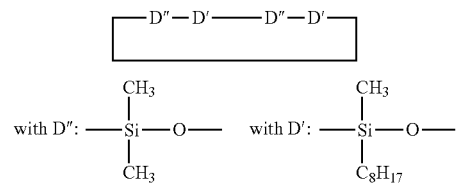

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m²/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers *Volatile Silicone Fluids for Cosmetics*.

Non-volatile polydialkylsiloxanes, polydialkylsiloxane gums and resins, polyorganosiloxanes modified with organofunctional groups above, and mixtures thereof, are preferably used.

These silicones are more particularly chosen from polydialkylsiloxanes, among which mention may be made mainly of polydimethylsiloxanes containing trimethyl-silyl end groups. The viscosity of the silicones is measured, for example, at 25° C. according to ASTM standard 445 Appendix C.

Among these polydialkylsiloxanes, mention may be made, in a non-limiting manner, of the following commercial products:
 the Silbione® oils of the 47 and 70 047 series or the Mirasil® oils sold by Rhodia, for instance the oil 70 047 V 500 000;
 the oils of the Mirasil® series sold by the company Rhodia;
 the oils of the 200 series from the company Dow Corning, such as DC200 with a viscosity of 60 000 mm/s;
 the Viscasil® oils from General Electric and certain oils of the SF series (SF 96, SF 18) from General Electric.

Mention may also be made of polydimethylsiloxanes containing dimethylsilanol end groups known under the name Dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly($C_1$-$C_{20}$)dialkylsiloxanes.

The silicone gums that may be used in accordance with the invention are especially polydialkylsiloxanes and preferably polydimethylsiloxanes with high number-average molecular masses of between 200 000 and 1 000 000, used alone or as a mixture in a solvent. This solvent may be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Products that may be used more particularly in accordance with the invention are mixtures such as:
 mixtures formed from a polydimethylsiloxane hydroxylated at the chain end, or dimethiconol (CTFA) and from a cyclic polydimethylsiloxane also known as cyclomethicone (CTFA), such as the product Q2 1401 sold by the company Dow Corning;
 mixtures formed from a polydimethylsiloxane gum with a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;
 mixtures of two PDMSs with different viscosities, and more particularly of a PDMS gum and a PDMS oil, such as the product SF 1236 from the company General Electric. The product SF 1236 is a mixture of an SE 30 gum defined above, having a viscosity of 20 $m^2$/s, and an SF 96 oil, with a viscosity of $5 \times 10^{-6}$ $m^2$/s. This product preferably contains 15% SE 30 gum and 85% SF 96 oil.

The organopolysiloxane resins that can be used in accordance with the invention are crosslinked siloxane systems containing the following units:
 $R_2SiO_{2/2}$, $R_3SiO_{1/2}$, $RSiO_{3/2}$ and $SiO_{4/2}$
in which R represents an alkyl containing 1 to 16 carbon atoms. Among these products, the ones that are particularly preferred are those in which R denotes a $C_1$-$C_4$ lower alkyl group, more particularly methyl.

Among these resins, mention may be made of the product sold under the name Dow Corning 593 or those sold under the names Silicone Fluid SS 4230 and SS 4267 by the company General Electric, which are silicones of dimethyl/trimethyl siloxane structure.

Mention may also be made of the trimethyl siloxysilicate type resins sold in particular under the names X22-4914, X21-5034 and X21-5037 by the company Shin-Etsu.

The organomodified silicones that may be used in accordance with the invention are silicones as defined above and comprising in their structure one or more organofunctional groups attached via a hydrocarbon-based group.

Besides the silicones described above, the organomodified silicones may be polydiarylsiloxanes, especially polydiphenylsiloxanes, and polyalkylarylsiloxanes functionalized with the organofunctional groups mentioned previously.

The polyalkylarylsiloxanes are particularly chosen from linear and/or branched polydimethyl/methylphenylsiloxanes and polydimethyl/diphenylsiloxanes with a viscosity of from $1 \times 10^{-5}$ to $5 \times 10^{-2}$ $m^2$/s at 25° C.

Among these polyalkylarylsiloxanes, examples that may be mentioned include the products sold under the following names:
 the Silbione® oils of the 70 641 series from Rhodia;
 the oils of the Rhodorsil® 70 633 and 763 series from Rhodia;
 the oil Dow Corning 556 Cosmetic Grade Fluid from Dow Corning;
 the silicones of the PK series from Bayer, such as the product PK20;
 the silicones of the PN and PH series from Bayer, such as the products PN1000 and PH1000;
 certain oils of the SF series from General Electric, such as SF 1023, SF 1154, SF 1250 and SF 1265.

Among the organomodified silicones, mention may be made of polyorganosiloxanes comprising:
 polyethyleneoxy and/or polypropyleneoxy groups optionally comprising $C_6$-$C_{24}$ alkyl groups, such as the products known as dimethicone copolyol sold by the company Dow Corning under the name DC 1248 or the oils Silwet® L 722, L 7500, L 77 and L 711 by the company Union Carbide, and the ($C_{12}$)alkylmethicone copolyol sold by the company Dow Corning under the name Q2 5200;
 substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups are, in particular, $C_1$-$C_4$ aminoalkyl groups;
 alkoxylated groups such as the product sold under the name Silicone Copolymer F-755 by SWS Silicones, and Abil Wax® 2428, 2434 and 2440 by the company Goldschmidt.

Preferably, the fatty substances are neither oxyalkylenated nor glycerolated.

More particularly, the fatty substances are chosen from compounds that are liquid or pasty at room temperature and at atmospheric pressure.

Preferably, the fatty substance is a compound that is liquid at a temperature of 25° C. and at atmospheric pressure.

The fatty substances are preferably chosen from $C_6$-$C_{16}$ lower alkanes, fatty alcohols, fatty acid esters, fatty alcohol esters, non-silicone oils of mineral origin containing more than 16 carbon atoms or of plant or synthetic origin, and silicones.

In particular, the fatty substance(s) of the dye composition that is useful in the context of the invention are non-silicone.

According to one embodiment of the invention, the fatty substance(s) are chosen from liquid petroleum jelly, polydecenes, and liquid esters of fatty acids or of fatty alcohols, or mixtures thereof. In particular, the fatty substance(s) of the composition according to the invention are non-silicone.

$C_6$-$C_{16}$ lower alkanes or hydrocarbons of more than 16 carbon atoms will preferably be chosen.

Liquid petroleum jelly is particularly preferred.

If they are present, the amount of fatty substance in the dye composition that is useful in the context of the invention is preferably between 1% and 75%, better still between 10% and 70% and even more preferentially between 20% and 65% by weight.

The suitable dyeing medium, also known as the dye support, is a cosmetic medium generally formed from water or from a mixture of water and one or more organic solvents. Examples of organic solvents that may be mentioned include $C_1$-$C_4$ lower alkanols, such as ethanol and isopropanol; polyols and polyol ethers, for instance 2-butoxyethanol, propylene glycol, propylene glycol monomethyl ether and diethylene glycol monomethyl ether and monoethyl ether, and also aromatic alcohols, for instance benzyl alcohol or phenoxyethanol, and mixtures thereof.

The solvents are preferably present in proportions preferably of between 1% and 40% by weight approximately and even more preferentially between 5% and 30% by weight approximately relative to the total weight of the dye composition.

The dye composition that is useful in the context of the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic or amphoteric polymeric associative thickeners, antioxidants, penetrants, sequestrants, fragrances, buffers, dispersants, conditioning agents, for instance volatile or non-volatile, modified or unmodified silicones, film-forming agents, ceramides, preserving agents and opacifiers.

The above adjuvants are generally present in an amount for each of them of between 0.01% and 20% by weight relative to the weight of the dye composition.

Needless to say, a person skilled in the art will take care to select this or these optional additional compound(s) such that the advantageous properties intrinsically associated with the oxidation dye composition in accordance with the invention are not, or are not substantially, adversely affected by the envisaged addition(s).

The pH of the dye composition that is useful in the context of the invention is generally between 3 and 12 approximately and preferably between 5 and 11 approximately. It may be adjusted to the desired value by means of acidifying or basifying agents usually used in the dyeing of keratin fibres, or alternatively using standard buffer systems.

Among the acidifying agents, examples that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

Among the basifying agents, examples that may be mentioned include aqueous ammonia, alkali metal carbonates, alkanolamines such as monoethanolamine, diethanolamine and triethanolamine, and also derivatives thereof, sodium hydroxide, potassium hydroxide and the compounds of the following formula:

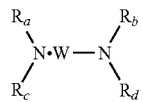

in which W is a propylene residue optionally substituted with a hydroxyl group or a $C_1$-$C_4$ alkyl radical; $R_a$, $R_b$, $R_c$ and $R_d$, which may be identical or different, represent a hydrogen atom, a $C_1$-$C_4$ alkyl radical or a $C_1$-$C_4$ hydroxyalkyl radical.

The dye composition that is useful in the context of the invention may be in various forms, such as in the form of liquids, creams or gels, or in any other form that is suitable for dyeing keratin fibres, and especially human hair.

The oxidizing composition that is useful in the context of the invention comprises one or more oxidizing agents.

More particularly, the oxidizing agent(s) are chosen from hydrogen peroxide, urea peroxide, alkali metal bromates or ferricyanides, peroxygenated salts, for instance persulfates and perborates, peracids and precursors thereof, and percarbonates of alkali metals or alkaline-earth metals such as sodium, potassium or magnesium.

The use of hydrogen peroxide is particularly preferred.

The oxidizing agent is advantageously formed from hydrogen peroxide, especially as an aqueous solution (aqueous hydrogen peroxide solution) whose titre may range, more particularly, from 1 to 40 volumes (i.e. 0.3% to 12% $H_2O_2$) and even more preferentially from 5 to 40 volumes (i.e. 1.5% to 12% $H_2O_2$).

The device in accordance with the invention may be equipped with a means for dispensing on the hair the composition(s) it contains, such as the devices described in patent FR-2 586 913 in the name of the Applicant.

Another subject of the invention is a process for dyeing keratin fibres, which consists in applying on the hair the composition(s) present in the device in accordance with the invention as described previously.

In accordance with a first embodiment, the composition applied does not comprise any oxidizing agent. This embodiment is especially suitable in the case where the composition does not comprise any oxidation dye precursors (bases or couplers).

In accordance with a second embodiment, the composition is applied in the presence of at least one oxidizing agent.

According to a first variant of this embodiment, the composition that is obtained by extemporaneous mixing, before application, of the dye composition free of oxidizing agent with the oxidizing composition is applied to the fibres.

According to a second variant of this embodiment, the dye composition free of oxidizing agent and the oxidizing composition are applied successively and without intermediate rinsing.

The oxidizing composition used comprises one or more oxidizing agents as defined above.

As regards the organic solvents that may be present in the oxidizing composition, reference may be made to the list given previously in the context of the description of the composition according to the invention.

Usually, the pH of the oxidizing composition is less than 7.

The oxidizing composition may be in the form of a solution, a gel or an emulsion.

It may optionally comprise one or more additives conventionally used in the field of dyeing human keratin fibres, as a function of the desired galenical form. Reference may be made, here also, to the list of additives given above.

In one variant of the invention, the composition obtained by extemporaneous mixing, before application, of the dye composition free of oxidizing agent with the oxidizing composition contains more than 20% by weight, preferably more than 25% and better still more than 30% of fatty substances as defined previously.

Irrespective of the embodiment adopted (with or without oxidizing agent), the mixture applied to the fibres is left in place for a time generally from about 1 minute to 1 hour and preferably from 10 minutes to 30 minutes.

The temperature during the process is conventionally between 10 and 200° C., more particularly between room temperature (between 15 and 25° C.) and 80° C., and preferably between room temperature and 60° C.

After the treatment, the human keratin fibres are optionally rinsed with water, washed with shampoo, rinsed again with water and then dried or left to dry.

A subject of the present invention is also the use for dyeing keratin fibres, and in particular human keratin fibres such as the hair, of a device as defined previously.

A subject of the present invention is also the use, for increasing the dissolution of the hair dyes in the dye composition, of one or more polycondensates of ethylene oxide and propylene oxide, consisting of polyethylene glycol and polypropylene glycol blocks as defined previously.

A second subject of the invention is an agent for dyeing and/or bleaching keratin fibres, and in particular human keratin fibres such as the hair, obtained by mixing a composition A comprising at least one alkaline agent with a composition B comprising at least one oxidizing agent, compositions A and/or B comprising at least one fatty substance free of carboxylic acid groups, at least one polycondensate of ethylene oxide and propylene oxide, and a nonionic surfactant system with a weighted HLB of greater than or equal to 8, the amount of fatty substance being greater than 20% by weight relative to the total weight of the dyeing and/or bleaching agent.

Composition A that is useful in the context of the present invention comprises one or more alkaline agents.

The alkaline agent(s) may be chosen from organic amines, mineral bases, salts of organic amines, ammonium salts and aqueous ammonia, and preferably from organic amines.

Examples of organic amines that may be mentioned include organic amines whose $pK_b$ at 25° C. is less than 12, preferably less than 10 and even more preferentially less than 6. It should be noted that it is the $pK_b$ corresponding to the function of highest basicity.

The organic amine may comprise one or two primary, secondary or tertiary amine functions, and one or more linear or branched $C_1$-$C_8$ alkyl groups bearing one or more hydroxyl radicals.

Organic amines chosen from alkanolamines such as mono-, di- or trialkanolamines comprising one to three identical or different $C_1$-$C_4$ hydroxyalkyl radicals are particularly suitable for use in the invention.

Among the compounds of this type, mention may be made of monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

Also suitable for use are organic amines having the following formula:

$$\begin{array}{c} Rx \\ \diagdown \\ Ry \end{array} N\text{-}W - N \begin{array}{c} Rz \\ \diagup \\ Rt \end{array}$$

in which W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom or a $C_1$-$C_6$ alkyl, $C_1$-$C_6$ hydroxyalkyl or $C_1$-$C_6$ aminoalkyl radical.

Examples of such amines that may be mentioned include 1,3-diaminopropane, 1,3-diamino-2-propanol, spermine and spermidine.

According to another variant of the invention, the organic amine is chosen from amino acids.

More particularly, the amino acids that may be used are of natural or synthetic origin, in their L, D or racemic form, and comprise at least one acid function more particularly chosen from carboxylic, sulfonic, phosphonic and phosphoric acid functions. The amino acids may be in neutral or ionic form.

Advantageously, the amino acids are basic amino acids comprising an additional amine function optionally included in a ring or in a ureido function.

Such basic amino acids are preferably chosen from those corresponding to formula (I) below:

$$R-CH_2-CH\begin{array}{c} NH_2 \\ \diagup \\ \diagdown \\ CO_2H \end{array} \qquad (I)$$

in which R denotes a group chosen from:

$$\begin{array}{c} \text{imidazole ring}; \quad -(CH_2)_3NH_2; \quad -(CH_2)_2NH_2; \\ -(CH_2)_2NHCONH_2; \quad -(CH_2)_2NH-\underset{\underset{NH}{\|}}{C}-NH_2 \end{array}$$

The compounds corresponding to formula (I) are histidine, lysine, arginine, ornithine and citrulline.

As amino acids that may be used in the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

According to one preferred variant of the invention, the organic amine is chosen from basic amino acids. The amino acids that are particularly preferred are arginine, lysine and histidine, or mixtures thereof.

According to another variant of the invention, the organic amine is chosen from organic amines of heterocyclic type. Besides histidine that has already been mentioned in the amino acids, mention may be made in particular of pyridine, piperidine, imidazole, 1,2,4-triazole, tetrazole and benzimidazole.

According to another variant of the invention, the organic amine is chosen from amino acid dipeptides. As amino acid dipeptides that may be used in the present invention, mention may be made especially of carnosine, anserine and baleine.

According to another variant of the invention, the organic amine is chosen from compounds comprising a guanidine function. As amines of this type that may be used in the present invention, besides arginine that has already been mentioned as an amino acid, mention may be made especially of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-[amino(imino)methyl]amino)ethane-1-sulfonic acid.

Preferably, the organic amine is an alkanolamine. More preferentially, the organic amine is chosen from 2-amino-2-methyl-1-propanol and monoethanolamine, or mixtures thereof. Even more preferentially, the organic amine is monoethanolamine.

The alkaline agent(s) may be an organic amine in salt form. For the purposes of the present invention, the term "salts of organic amines" means the organic or mineral salts of an organic amine as described above.

Preferably, the organic salts are chosen from organic acid salts such as citrates, lactates, glycolates, gluconates, acetates, propionates, fumarates, oxalates and tartrates.

Preferably, the mineral salts are chosen from hydrohalides (for example hydrochlorides), carbonates, hydrogen carbonates, sulfates, hydrogen phosphates and phosphates.

For the purposes of the present invention, the term "mineral compound" means any compound bearing in its structure one or more elements from columns 1 to 13 of the Periodic Table of the Elements other than hydrogen, not simultaneously comprising carbon and hydrogen atoms.

According to one particular embodiment of the invention, the mineral base contains one or more elements from columns 1 and 2 of the Periodic Table of the Elements other than hydrogen.

In one preferred variant, the mineral base has the following structure:

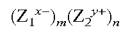

in which:
$Z_2$ denotes a metal from columns 1 to 13 and preferably from column 1 or 2 of the Periodic Table of the Elements, for instance sodium or potassium;
$Z_1^{x-}$ denotes an anion chosen from the ions $CO_3^{2-}$, $OH^-$, $HCO_3^{2-}$, $SiO_3^{2-}$, $HPO_4^{2-}$, $PO_4^{3-}$ and $B_4O_7^{2-}$, and preferably from the ions $CO_3^{2-}$, $OH^-$ and $SiO_3^{2-}$;
x denotes 1, 2 or 3;
y denotes 1, 2, 3 or 4;
m and n independently denote 1, 2, 3 or 4;
with $n \cdot y = m \cdot x$.

Preferably, the mineral base corresponds to the following formula $(Z_1^{x-})_m(Z_2^{y+})_n$, in which $Z_2$ denotes a metal from columns 1 and 2 of the Periodic Table of the Elements; $Z_1^{x-}$ denotes an anion chosen from the ions $CO_3^{2-}$, $OH^-$ and $SiO_3^{2-}$, x is 1, y denotes 1 or 2, m and n independently denote 1 or 2 with $n \cdot y = m \cdot x$.

As mineral bases that may be used according to the invention, mention may be made of sodium carbonate, potassium carbonate, sodium hydroxide, potassium hydroxide, sodium metasilicate and potassium metasilicate.

Ammonium salts may also be used as alkaline agent.

The ammonium salts that may be used in composition A that is useful in the context of the present invention are the ammonium ($NH_4^+$) salts.

The ammonium salts that may be used in composition A that is useful in the context of the present invention are preferably chosen from the following acid salts: acetate, carbonate, bicarbonate, chloride, citrate, nitrate, nitrite, phosphate, sulfate. In a particularly preferred manner, the salt is the carbonate, such as ammonium carbonate.

Preferably, the alkaline agent(s) are chosen from organic amines.

Generally, composition A that is useful in the context of the invention has a content of alkaline agents ranging from 0.1% to 40% by weight and preferably from 0.5% to 20% by weight relative to the total weight of the said composition.

According to one preferred embodiment of the invention, the weight amount of alkanolamine is greater than the weight amount of aqueous ammonia in composition A.

Composition A is generally an aqueous composition.

According to one particular embodiment, the water concentration may range from 5% to 70% and better still from 10% to 50% of the total weight of composition A.

According to another particular embodiment, the concentration of the aqueous phase (comprising water and the compounds that are soluble in water at room temperature and at atmospheric pressure) may range from 10% to 70% and better still from 15% to 50% of the total weight of composition A.

Finally, composition A is in various forms, for instance in the form of a solution, an emulsion or a gel.

Composition B that is useful in the context of the present invention comprises one or more oxidizing agents.

More particularly, the oxidizing agent(s) are as defined previously.

The concentration of oxidizing agents in composition B generally ranges from 0.1% to 20% by weight and preferably from 0.5% to 10% by weight relative to the total weight of the said composition.

Depending on the desired degree of lightening, the oxidizing agent may also comprise an oxidizing agent preferably chosen from peroxygenated salts.

Composition B is generally an aqueous composition. In the case where composition B also comprises an oxidizing agent chosen from peroxygenated salts, it is generally obtained by mixing an anhydrous composition comprising the peroxygenated salt(s) with an aqueous composition comprising hydrogen peroxide.

The pH of composition B may range from 2 to 12. Usually, the pH of composition B is less than 7. It may be adjusted to the desired value by means of acidifying or basifying agents usually used in the dyeing of keratin fibres, or alternatively using standard buffer systems.

The alkaline agents are, for example, those described previously.

Among the acidifying agents, examples that may be mentioned include mineral or organic acids, for instance hydrochloric acid, orthophosphoric acid or sulfuric acid, carboxylic acids, for instance acetic acid, tartaric acid, citric acid or lactic acid, and sulfonic acids.

Finally, composition B is in various forms, for instance in the form of a solution, an emulsion or a gel.

Compositions A and/or B that are useful in the context of the present invention comprise one or more fatty substances free of carboxylic acid groups, such as those described previously.

Preferably, the concentration of fatty substance in compositions A and/or B of the invention may range from 5% to 90%, preferably from 10% to 75%, even more preferentially from 20% to 60%, better still from 30% to 55% and even better still from 35% to 55% relative to the total weight of the said composition.

The amount of fatty substance in the agent for dyeing and/or bleaching keratin fibres in accordance with the invention resulting from the mixing of compositions A and B is greater than 20% by weight, preferably ranging from 20.5% to 75% by weight, of the dyeing and/or bleaching agent. Even more preferentially, the amount of fatty substance is greater than 25% by weight, preferably ranging from 25.5% to 75% by weight of the dyeing and/or bleaching agent. Better still, the amount of fatty substance is greater than 30%, preferably ranging from 30.5% to 75% by weight of the dyeing and/or bleaching agent.

Compositions A and/or B comprise a polycondensate of ethylene oxide and propylene oxide, and more particularly a copolymer consisting of polyethylene glycol and polypropylene glycol blocks as described previously.

The polycondensate of ethylene oxide and propylene oxide may be present in the dyeing and/or bleaching agent according to the invention in a content ranging from 0.01% to 5% by weight, preferably ranging from 0.05% to 3% by weight and more preferentially ranging from 0.05% to 1% by weight relative to the total weight of the dyeing and/or bleaching agent.

Compositions A and/or B comprise a system of one or more nonionic surfactants other than polycondensates of ethylene oxide and propylene oxide, with a weighted HLB of greater than 8.

The HLB reflects the ratio between the hydrophilic part and the lipophilic part in the molecule of a nonionic surfactant. This term HLB is well known to those skilled in the art and is described in *The HLB system. A time-saving guide to emulsifier selection* (published by ICI Americas Inc.; 1984).

For the purposes of the present invention, the term "weighted HLB" means the average of the HLB values of the various nonionic surfactants present in the composition weighted on the basis of their respective weight amount.

The nonionic surfactants that may be used in the compositions of the present invention are compounds that are well known per se (see especially in this regard the *Handbook of Surfactants* by M. R. Porter, published by Blackie & Son (Glasgow and London), 1991, pp. 116-178). They are especially chosen from polyethoxylated, polypropoxylated or polyglycerolated alcohols, α-diols, ($C_{1-20}$)alkylphenols and fatty acids, bearing a fatty chain comprising, for example, from 8 to 18 carbon atoms, the number of ethylene oxide or propylene oxide groups possibly ranging especially from 2 to 50 and the number of glycerol groups possibly ranging especially from 2 to 30.

Mention may also be made of condensates of ethylene oxide and of propylene oxide with fatty alcohols; polyethoxylated fatty amides preferably containing from 2 to 30 ethylene oxide units, polyglycerolated fatty amides comprising on average from 1 to 5 glycerol groups and in particular from 1.5 to 4 glycerol groups, ethoxylated fatty acid esters of sorbitan containing from 2 to 30 ethylene oxide units, fatty acid esters of sucrose, fatty acid esters of polyethylene glycol, ($C_{6-24}$ alkyl)polyglucosides, N—($C_{6-24}$ alkyl)glucamine derivatives, and amine oxides such as ($C_{10-14}$ alkyl)amine oxides or N—($C_{10-14}$ acyl)aminopropylmorpholine oxides.

According to one preferred embodiment, the nonionic surfactants other than polycondensates of ethylene oxide and propylene oxide are chosen from oxyalkylenated surfactants and non-oxyalkylenated monoglycerolated or polyglycerolated surfactants. Preferably, the nonionic surfactants other than polycondensates of ethylene oxide and propylene oxide are chosen from oxyalkylenated surfactants.

For the purposes of the present invention, the term "non-oxyalkylenated monoglycerolated or polyglycerolated nonionic surfactant" means a nonionic surfactant comprising in its structure one or more units —$CH_2$—$CH(CH_2OH)$—O— and not comprising any units of the type —Z—O—, Z denoting an unsubstituted linear or branched alkylene radical, such as —$CH_2$—$CH_2$—, —$CH_2$—$CH_2$—$CH_2$— or —$CH_2$—CH($CH_3$)—.

The non-oxyalkylenated monoglycerolated or polyglycerolated nonionic surfactant(s) that may be used according to the invention are preferably chosen from non-oxyalkylenated monoglycerolated or polyglycerolated fatty alcohols and fatty esters.

More preferentially, the non-oxyalkylenated monoglycerolated or polyglycerolated nonionic surfactant(s) that may be used in the compositions of the invention are chosen from non-oxyalkylenated monoglycerolated or polyglycerolated fatty alcohols.

In a particularly preferred manner, the non-oxyalkylenated monoglycerolated or polyglycerolated surfactant(s) that may be used in the compositions according to the invention correspond to the general formula (V) below:

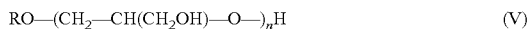

RO—($CH_2$—CH($CH_2OH$)—O—)$_n$H    (V)

in which:

R represents a linear or branched, saturated or unsaturated radical comprising from 8 to 40 carbon atoms, preferably from 10 to 30 carbon atoms and better still from 10 to 20 carbon atoms;

n represents a number ranging from 1 to 30, preferably from 1 to 10 and better still from 1 to 5.

The non-oxyalkylenated monoglycerolated or polyglycerolated nonionic surfactants that may be used in the compositions of the invention may be present alone or as a mixture. In the case of a mixture, the value of n of formula (V) above represents a statistical value, which means that, in a commercial product, several species of non-oxyalkylenated monoglycerolated or polyglycerolated nonionic surfactants, for instance non-oxyethylenated monoglycerolated or polyglycerolated fatty alcohols, may coexist in the form of a mixture.

As more specific examples of non-oxyalkylenated glycerolated nonionic surfactants that may be used in the compositions of the invention, mention may be made, inter alia, of lauryl alcohol containing 4 mol of glycerol (INCI name: polyglyceryl-4 lauryl ether), lauryl alcohol containing 1.5 mol of glycerol (INCI name: glyceryl lauryl ether), oleyl alcohol containing mol of glycerol (INCI name: polyglyceryl-4 oleyl ether), oleyl alcohol containing 2 mol of glycerol (INCI name: polyglyceryl-2 oleyl ether), cetearyl alcohol containing 2 mol of glycerol, cetearyl alcohol containing 6 mol of glycerol, oleocetyl alcohol containing 6 mol of glycerol and octadecanol containing 6 mol of glycerol.

Preferably, the non-oxyalkylenated glycerolated nonionic surfactants of the invention are monoglycerolated or polyglycerolated lauryl alcohols.

Among the oxyalkylenated nonionic surfactants with an HLB of greater than 5, mention may be made in a non-limiting manner of the compounds belonging to the following families:

oxyethylenated alkylphenols containing more than 2 mol of OE, oxyethylenated plant oils containing more than 5 mol of OE, oxyethylenated fatty alcohols containing more than 2 mol of OE, fatty acid esters of polyethylene glycols, polyoxyethylenated fatty acid esters of sorbitol.

Commercial compounds that may especially be mentioned include:

| | | |
|---|---|---|
| Imbentin POA/024 | (HLB = 5.5) | (ICI) |
| Mergital LM2 | (HLB = 5.8) | (Henkel) |
| Atlas G-70140 | (HLB = 6) | (ICI) |
| Imbentin AG/124S/020 | (HLB = 6) | (Kolb) |
| Imbentin L/125/025 | (HLB = 6) | (Kolb) |
| Simulsol 989 | (HLB = 6) | (SEPPIC) |
| Soprophor HR10 | (HLB = 6) | (Rhône-Poulenc) |
| Kotilen O/1/050 | (HLB = 6.2) | (Kolb) |
| Croduret 10 | (HLB = 6.3) | (Croda) |
| Etocas 10 | (HLB = 6.3) | (Croda) |
| Imbentin OA/030 | (HLB = 6.3) | (Kolb) |
| Soprophor 208 | (HLB = 6.9) | (Rhône-Poulenc) |
| Ethylan 172 | (HLB = 7) | (Harcros) |
| Akyporox NP 40 | (HLB = 7.1) | (Chem-Y) |
| Polychol 5 | (HLB = 7.3) | (Croda) |
| Arlatone 985 | (HLB = 7.5) | (ICI) |
| Sandoxylate FOL4 | (HLB = 7.5) | (Sandoz) |
| Radiasurf 7453 | (HLB = 7.8) | (Oleofina) |
| Prox-onic OA-1/04 | (HLB = 7.9) | (Protex) |
| Prox-onic TD-1/03 | (HLB = 7.9) | (Protex) |
| Genapol PF 40 | (HLB = 8) | (Hoechst) |
| PGE-400-DS | (HLB = 8) | (Hefti) |
| PGE-400-DO | (HLB = 8) | (Hefti) |
| Sapogenat 6-040 | (HLB = 8) | (Hoechst) |
| Intrasol FA28/50/4 | (HLB = 8.1) | (Stockhausen) |
| Serdox NOG 200 S | (HLB = 8.5) | (Servo) |
| Berol 26 | (HLB = 8.9) | (Berol Nobel) |
| Genapol O-050 | (HLB = 9) | (Hoechst) |
| Prox-onic LA-1/04 | (HLB = 9.2) | (Protex) |
| Eumulgin O5 | (HLB = 9.5) | (Henkel) |
| Etocas 20 | (HLB = 9.6) | (Croda) |
| Antarox CO 520 | (HLB = 10) | (Rhône-Poulenc) |
| Imbentin POA/060 | (HLB = 10) | (Kolb) |
| TO-55-EL | (HLB = 10) | (Hefti) |
| Atlas G-1086 | (HLB = 10.2) | (ICI) |
| Atlox 4878B | (HLB = 10.5) | (ICI) |
| Berol 059 | (HLB = 10.5) | (Berol Nobel) |
| Kessco PEG 600 Dilaurate | (HLB = 10.5) | (Akzo) |
| Mergital LT6 | (HLB = 10.6) | (Henkel) |
| Polychol 10 | (HLB = 10.7) | (Croda) |
| Prox-onic HR-025 | (HLB = 10.8) | (Protex) |
| Tebenal NP6 | (HLB = 10.9) | (Bohme) |
| Cremophor A6 | (HLB = 11) | (BASF) |
| Genapol O-080 | (HLB = 11) | (Hoechst) |
| Genapol T-080 | (HLB = 11) | (Hoechst) |
| Kotilen-O/3 | (HLB = 11) | (Kolb) |
| Lutensol AP 7 | (HLB = 11) | (BASF) |
| Tween 85 | (HLB = 11) | (ICI) |
| Tebecid S8 | (HLB = 11.2) | (Bohme) |
| Berol 047 | (HLB = 11.4) | (Berol Nobel) |
| Soprophor 860P | (HLB = 11.4) | (Rhône-Poulenc) |
| Dobanol 45-7 | (HLB = 11.6) | (Shell) |
| Prox-onic HR-030 | (HLB = 11.7) | (Protex) |
| Ethonic 1214-6.5 | (HLB = 11.8) | (Ethyl) |
| Prox-onic OA-1/09 | (HLB = 11.9) | (Protex) |
| Cremophor S9 | (HLB = 12) | (BASF) |
| Imbentin AG/128/080 | (HLB = 12) | (Kolb) |
| Serdox NOG 440 | (HLB = 12) | (Servo) |
| Softanol 70 | (HLB = 12.1) | (B.P. Chemicals) |
| Renex 707 | (HLB = 12.2) | (ICI) |
| Simulsol 830 NP | (HLB = 12.3) | (SEPPIC) |
| Brij 76 | (HLB = 12.4) | (ICI) |
| Tebenal T10 | (HLB = 12.4) | (Bohme) |
| Volpo S-10 | (HLB = 12.4) | (Croda) |
| Eumulgin O10 | (HLB = 12.5) | (Henkel) |
| Berol 199 | (HLB = 12.6) | (Berol Nobel) |
| Triton N-87 | (HLB 12.6) | (Rohm & Haas) |
| Polychol 15 | (HLB = 12.7) | (Croda) |
| Brij 56 | (HLB = 12.9) | (ICI) |
| Simulsol 56 | (HLB = 12.9) | (SEPPIC) |
| Cremophor A11 | (HLB = 13) | (BASF) |
| Eumulgin 286 | (HLB = 13) | (Henkel) |
| Genapol T-110 | (HLB = 13) | (Hoechst) |
| Sandoxylate FOL12 | (HLB = 13) | (Sandoz) |
| Bio Soft HR 40 | (HLB = 13.1) | (Stepan) |
| Berol 046 | (HLB = 13.5) | (Berol Nobel) |
| Eumulgin B1 | (HLB = 13.5) | (Henkel) |
| Dobanol 45-11 | (HLB = 13.7) | (Shell) |
| Aqualose W20 | (HLB = 14) | (Westbrook Lanolin) |
| Ethylan DP | (HLB = 14) | (Harcros) |
| Mergital OC12 | (HLB = 14) | (Henkel) |
| Simulsol 1230 NP | (HLB = 14) | (SEPPIC) |
| Tagat R1 | (HLB = 14) | (Goldschmidt) |
| Tagat I 2 | (HLB = 14.2) | (Goldschmidt) |
| Tebecid RM20 | (HLB = 14.4) | (Bohme) |
| Imbentin AG/168/150 | (HLB = 14.5) | (Kolb) |
| Prox-onic LA-1/012 | (HLB = 14.5) | (Protex) |
| Etocas 60 | (HLB = 14.7) | (Croda) |
| Radiasurf 7157 | (HLB = 14.9) | (Oleofina) |
| Genapol T-180 | (HLB = 15) | (Hoechst) |
| Montanox 80 | (HLB = 15) | (SEPPIC) |
| Serdox NJAD 20 | (HLB = 15) | (Servo) |
| Tagat R60 | (HLB = 15) | (Goldschmidt) |
| Berol 278 | (HLB = 15.2) | (Berol Nobel) |
| Brij 78 | (HLB = 15.3) | (ICI) |
| Simulsol 98 | (HLB = 15.3) | (SEPPIC) |
| Montanox 40 | (HLB = 15.6) | (SEPPIC) |
| Brij 58 | (HLB = 15.7) | (ICI) |
| Aqualose L75 | (HLB = 16) | (Westbrook Lanolin) |
| Atlas G-1471 | (HLB = 16) | (ICI) |
| Berol 281 | (HLB = 16) | (Berol Nobel) |
| Berol 292 | (HLB = 16) | (Berol Nobel) |
| Nafolox 20-22 30OE | (HLB = 16) | (Condea) |
| Genapol C-200 | (HLB = 16) | (Hoechst) |
| Myrj 51 | (HLB = 16) | (ICI) |
| Simulsol PS 20 | (HLB = 16) | (SEPPIC) |
| Tergitol 15 S 20 | (HLB 16.3) | (Union Carbide) |
| Montanox 20 | (HLB = 16.7) | (SEPPIC) |
| Myrjj 52 | (HLB = 16.9) | (ICI) |
| Simulsol 3030 NP | (HLB = 17) | (SEPPIC) |
| Imbentin AG/168/400 | (HLB = 17.5) | (Kolb) |
| Rhodia Surf NP40 | (HLB = 17.7) | (Rhône-Poulenc) |
| Incropol CS-50 | (HLB = 17.9) | (Croda) |
| Servirox OEG 90/50 | (HLB = 18) | (Servo) |
| Prox-onic HR-0200 | (HLB = 18.1) | (Protex) |
| Berol 243 | (HLB = 18.2) | (Berol Nobel) |
| Imbentin N/600 | (HLB = 18.5) | (Kolb) |
| Antarox CO 980 | (HLB = 18.7) | (Rhône-Poulenc) |
| Antarox CO 987 | (HLB = 18.7) | (Rhône-Poulenc) |
| Berol 08 | (HLB = 18.7) | (Berol Nobel) |
| Brij 700 | (HLB = 18.8) | (ICI) |
| Prox-onic NP-0100 | (HLB = 19) | (Protex) |
| Rs-55-100 | (HLB = 19) | (Hefti) |
| Imbentin AG/168S/950 | (HLB = 20) | (Kolb) |
| Alkasurf BA-PE80 | (HLB = 26.1) | (Rhône-Poulenc) |

Among the oxyalkylenated nonionic surfactants with an HLB of less than or equal to 5, mention may be made in a non-limiting manner of:

oxyethylenated alkylphenols containing not more than 2 mol of OE, oxyethylenated plant oils containing not more than 5 mol of OE, oxyethylenated fatty alcohols containing not more than 2 mol of OE.

Commercial compounds that may especially be mentioned include:

| | | |
|---|---|---|
| Prox-Onic EP 4060-1 | (HLB = 1) | Protex |
| Etocas 29 | (HLB = 1.7) | Croda |
| Genapol PF 10 | (HLB = 2) | Hoechst |
| Prox-Onic EP 1090-1 | (HLB = 3) | Protex |
| Sinnopal DPN2 | (HLB = 3.3) | Henkel |
| Antarox CA 210 | (HLB = 3.5) | Rhône-Poulenc |
| Alkasurf OP11 | (HLB = 3.6) | Rhône-Poulenc |
| Triton X15 | (HLB = 3.6) | Rohm & Haas |
| Alkasurf OP1 | (HLB = 3.6) | Rhône-Poulenc |
| Arlacel 121 | (HLB = 3.8) | ICI |
| Prox-Onic HR or HRH-05 | (HLB = 3.8) | Protex |
| Etocas 5 | (HLB = 3.9) | Hoechst |
| Genapol PF20 | (HLB = 4) | Hoechst |
| Imbentin N/7 A | (HLB = 4) | Kolb |
| Ethylan NP1 | (HLB = 4.5) | Harcros |
| Imbentin N/020 | (HLB = 4.5) | Kolb |

| | | |
|---|---|---|
| Kotilen O/3/020 | (HLB = 4.5) | Kolb |
| TO-55-A | (HLB = 4.5) | Hefti |
| Alkasurf NP-1 | (HLB = 4.6) | Rhône-Poulenc |
| Antarox CO 210 | (HLB = 4.6) | Rhône-Poulenc |
| Prox-Onic NP-1 | (HLB = 4.6) | Protex |
| Rhodiasurf NP2 | (HLB = 4.6) | Rhône-Poulenc |
| Soprophor BC2 | (HLB = 4.6) | Rhône-Poulenc |
| Triton N17 | (HLB = 4.6) | Rohm & Haas |
| Akyporox NP15 | (HLB = 4.7) | Chem-Y |
| Texofor M2 | (HLB = 4.8) | Rhône-Poulenc |
| Alkasurf SA2 | (HLB = 4.9) | Rhône-Poulenc |
| Arlacel 989 | (HLB = 4.9) | ICI |
| Brij 72 | (HLB = 4.9) | ICI |
| Brij 92 | (HLB = 4.9) | ICI |
| Brij 93 | (HLB = 4.9) | ICI |
| Prox-Onic SA-1 or 2/02 | (HLB = 4.9) | Protex |
| Simulsol 72 | (HLB = 4.9) | SEPPIC |
| Simulsol 92 | (HLB = 4.9) | SEPPIC |
| Volpo S-2 | (HLB = 4.9) | Croda |
| Arlacel 581 | (HLB = 5.0) | ICI |
| Arlacel 582 | (HLB = 5.0) | ICI |
| Genapol O-020 | (HLB = 5.0) | Hoechst |
| Imbentin POA/020 | (HLB = 5.0) | Kolb |
| Mergital Q2 | (HLB = 5.0) | Henkel |

The concentration of these nonionic surfactants leading to a weighted HLB of greater than or equal to 8 may range from about 0.1% to 30%, preferably from about 0.5% to 25% and even more preferentially from about 1% to 20% by weight relative to the total weight of the dyeing and/or bleaching agent.

The surfactant(s) present in the treating agent in accordance with the invention are chosen such that the weighted HLB of the nonionic surfactant system is greater than or equal to 8. Preferably, the weighted HLB of the nonionic surfactant system is between 8 and 18 and more preferentially between 11 and 14.

According to one particular embodiment, all the non-ionic surfactants present in the dyeing and/or bleaching agent have an HLB of greater than or equal to 8.

Compositions A and/or B may comprise one or more surfactants other than the nonionic surfactants described previously. These additional surfactants may be anionic, amphoteric, zwitterionic or cationic.

As examples of anionic surfactants that may be used, alone or as mixtures, in the context of the present invention, mention may be made in particular (non-limiting list) of salts (in particular alkali metal salts, especially sodium salts, ammonium salts, amine salts, amino alcohol salts or magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; ($C_6$-$C_{24}$)alkyl sulfosuccinates, ($C_6$-$C_{24}$)alkyl ether sulfosuccinates, ($C_6$-$C_{24}$)alkylamide sulfosuccinates; ($C_6$-$C_{24}$)alkyl sulfoacetates; ($C_6$-$C_{24}$) acyl sarcosinates; and ($C_6$-$C_{24}$)acyl glutamates. It is also possible to use ($C_6$-$C_{24}$)alkylpolyglycoside carboxylic esters such as alkylglucoside citrates, alkylpolyglycoside tartrates and alkylpolyglycoside sulfosuccinates, alkyl-sulfosuccinamates; acyl isethionates and N-acyl taurates, the alkyl or acyl radical of all of these different compounds preferably containing from 12 to 20 carbon atoms and the aryl radical preferably denoting a phenyl or benzyl group. Among the anionic surfactants which can also be used, mention may also be made of fatty acid salts such as oleic, ricinoleic, palmitic and stearic acid salts, coconut oil acid or hydrogenated coconut oil acid; acyl lactylates in which the acyl radical contains 8 to 20 carbon atoms. It is also possible to use alkyl D-galactoside uronic acids and their salts, polyoxyalkylenated ($C_6$-$C_{24}$)alkyl ether carboxylic acids, polyoxyalkylenated ($C_6$-$C_{24}$)alkylaryl ether carboxylic acids, polyoxyalkylenated ($C_6$-$C_{24}$)alkylamido ether carboxylic acids and their salts, in particular those containing from 2 to 50 alkylene oxide groups, in particular ethylene oxide groups, and mixtures thereof.

The amphoteric or zwitterionic surfactants, the nature of which is not a critical factor in the context of the present invention, can be, in particular (non-limiting list), aliphatic secondary or tertiary amine derivatives in which the aliphatic radical is a linear or branched chain containing 8 to 18 carbon atoms and containing at least one water-solubilizing anionic group (for example carboxylate, sulfonate, sulfate, phosphate or phosphonate); mention may also be made of ($C_8$-$C_{20}$) alkylbetaines, sulfobetaines, ($C_8$-$C_{20}$)alkyl-amido($C_1$-$C_6$) alkylbetaines or ($C_8$-$C_{20}$)alkylamido ($C_1$-$C_6$)-alkylsulfobetaines.

Among the amine derivatives, mention may be made of the products sold under the name Miranol, as described in U.S. Pat. Nos. 2,528,378 and 2,781,354 and classified in the CTFA dictionary, 3rd edition, 1982, under the names Amphocarboxyglycinates and Amphocarboxypropionates, with the respective structures:

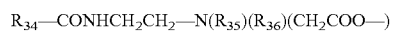

in which: $R_{34}$ denotes an alkyl radical of an acid $R_{34}$—COOH present in hydrolysed coconut oil, a heptyl, nonyl or undecyl radical, $R_{35}$ denotes a β-hydroxyethyl group and $R_{36}$ denotes a carboxymethyl group;

and

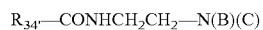

in which:

B represents —$CH_2CH_2OX'$, C represents —$(CH_2)_z$—Y', with z=1 or 2,

X' denotes the —$CH_2CH_2$—COOH group or a hydrogen atom,

Y' denotes —COOH or the —$CH_2$—CHOH—$SO_3H$ radical, $R_{34'}$ denotes an alkyl radical of an acid $R_{37}$—COOH present in coconut oil or in hydrolysed linseed oil, an alkyl radical, in particular a $C_7$, $C_9$, $C_{11}$ or $C_{13}$ alkyl radical, a $C_{17}$ alkyl radical and its iso form, or an unsaturated $C_{17}$ radical.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Capryloamphodipropionate, Lauroamphodipropionic acid and Cocoamphodipropionic acid.

By way of example, mention may be made of the cocoamphodiacetate sold under the trade name Miranol® C2M Concentrate by the company Rhodia Chimie.

Among the cationic surfactants, mention may be made in particular (non-limiting list) of: salts of optionally polyoxyalkylenated primary, secondary or tertiary fatty amines; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature.

The amounts of the additional surfactants present in the dyeing and/or bleaching agent according to the invention may range from 0.01% to 40% and preferably from 0.1% to 30% by weight relative to the total weight of the dyeing and/or bleaching agent.

According to one particular embodiment, all the surfactants present in compositions A and/or B that are useful in the context of the invention are chosen from nonionic surfactants.

According to a first preferred embodiment of the invention, the polycondensate(s) of ethylene oxide and propylene oxide are present in composition A.

According to a second preferred embodiment of the invention, the polycondensate(s) of ethylene oxide and propylene oxide and all or some of the nonionic surfactant system with a weighted HLB of greater than or equal to 8 are present in composition A.

According to a third preferred embodiment of the invention, the polycondensate(s) of ethylene oxide and propylene oxide, all or some of the nonionic surfactant system with a weighted HLB of greater than or equal to 8 and all or some of the fatty substances(s) free of carboxylic acid groups are present in composition A.

When the treating agent in accordance with the invention is an agent for dyeing keratin fibres, compositions A and/or B, and preferably solely composition A, comprise one or more colouring or coloured species chosen from oxidation dye precursors, synthetic direct dyes and natural dyes as described previously.

The oxidation base(s), if they are present, advantageously represents in each case from 0.0001% to 10% by weight and preferably from 0.005% to 5% by weight relative to the total weight of composition A and/or B.

The content of coupler(s), if they are present, advantageously represents in each case from 0.0001% to 10% by weight and preferably from 0.005% to 5% by weight relative to the total weight of composition A and/or B.

When they are present, the synthetic direct dye(s) more particularly represent from 0.0001% to 10% by weight and preferably from 0.005% to 5% by weight relative to the total weight of composition A and/or B.

The natural dyes, when they are present, generally represent from 0.001% to 10% by weight, preferably from 0.01% to 8% by weight and better still from 0.1% to 5% by weight relative to the weight of the composition.

Preferably, the composition according to the invention comprises one or more oxidation dyes.

According to one preferred embodiment of the invention, the colouring or coloured species are present in composition A.

Compositions A and/or B that are useful in the context of the invention may also contain various adjuvants conventionally used in hair treatment compositions, such as anionic, cationic, nonionic, amphoteric or zwitterionic polymers or mixtures thereof; mineral thickeners, and in particular fillers such as clays or talc; organic thickeners, in particular with anionic, cationic, nonionic and amphoteric polymeric associative thickeners; antioxidants; penetrants; sequestrants; fragrances; dispersants; film-forming agents; preserving agents; opacifiers.

Compositions A and/or B may optionally comprise one or more organic solvents. Examples of organic solvents that may be mentioned include linear or branched $C_2$-$C_4$ alkanols, such as ethanol and isopropanol; glycerol; polyols and polyol ethers such as 2-butoxyethanol, propylene glycol, dipropylene glycol, propylene glycol monomethyl ether, glycerol and diethylene glycol monomethyl ether and monoethyl ether, and also aromatic alcohols, for instance benzyl alcohol or phenoxyethanol, and mixtures thereof.

Needless to say, a person skilled in the art will take care to select the optional adjuvant(s) mentioned above, such that the advantageous properties intrinsically associated with the compositions according to the invention are not, or are not substantially, adversely affected by the envisaged addition(s).

The agent for dyeing and/or bleaching keratin fibres in accordance with the present invention is generally an aqueous composition. Its pH is generally between 3 and 12 approximately, preferably between 5 and 11 approximately and preferentially 7 to 11.

The dyeing and/or bleaching agent according to the invention may be in various forms, such as in the form of liquids, creams or gels, or in any other form that is suitable for dyeing keratin fibres, and especially human hair.

A subject of the present invention is also a process for dyeing and/or bleaching keratin fibres using the dyeing and/or bleaching agent described above.

The process of the invention may be performed by applying composition A and composition B successively and without intermediate rinsing.

According to another variant, a composition obtained by extemporaneous mixing, at the time of use, of composition A and composition B is applied to wet or dry keratin fibres.

According to this embodiment, the weight ratio of the amounts of A/B ranges from 0.1 to 10, preferably from 0.2 to 3 and better still from 0.3 to 1.

In addition, independently of the variant used, the mixture present on the keratin fibres (resulting either from the extemporaneous mixing of A and B or from their partial or total successive application) is left on for a time generally from about 1 minute to 1 hour and preferably from 5 minutes to 30 minutes.

The temperature during the process is conventionally between room temperature (between 15 and 25° C.) and 80° C. and preferably between room temperature and 60° C.

After treatment, the keratin fibres are optionally rinsed with water, and optionally undergo washing followed by rinsing with water, and are then dried or left to dry.

Finally, the invention relates to the use, for dyeing and/or bleaching keratin fibres, of a dyeing and/or bleaching agent as defined previously.

The examples that follow serve to illustrate the invention without, however, being limiting in nature.

EXAMPLES

Example 1

The following dye compositions were prepared (amounts expressed as grams of commercial product):

| Composition | A | B |
|---|---|---|
| para-Aminophenol | 3.05 | 3.05 |
| Resorcinol | 1.1 | 1.1 |
| 2-Methyl-5-hydroxyethylaminophenol | 5.24 | 5.24 |
| 4-Amino-2-hydroxytoluene | 1.74 | 1.74 |
| Toluene-2,5-diamine | 2.12 | 2.12 |
| Propylene glycol | 6.2 | 6.2 |
| Ethanol | 8.8 | 8.8 |
| Hexylene glycol | 3 | 3 |
| Dipropylene glycol | 3 | 3 |
| Pure monoethanolamine | 14.5 | 14.5 |
| Ascorbic acid | 0.25 | 0.25 |

41
-continued

| Composition | A | B |
|---|---|---|
| Demineralized water | 30 | 51 |
| Ethylene oxide/propylene oxide/ethylene oxide condensate (MW = 2900 g/mol) (13 EO/30 PO/13 EO) or Poloxamer 184 | 21 | 0 |

Composition B not containing any polycondensate of ethylene oxide and propylene oxide forms a precipitate after a few hours at room temperature. On the other hand, composition A containing a polycondensate of ethylene oxide and propylene oxide remains clear, even after two months at 45° C.

Compositions C and D below are also prepared (the amounts are expressed as g % of active materials):

| Composition | |
|---|---|
| | C |
| Disteardimonium hectorite (Bentone 38 VCG) | 3 |
| Octyldodecanol | 11.5 |
| Glycol distearate | 8 |
| Liquid petroleum jelly | 64.5 |
| Propylene carbonate | 1 |
| Laureth-2 | 1 |
| Polysorbate 21 | 11 |
| | D |
| Pentasodium pentetate | 0.15 |
| Hydrogen peroxide (aqueous 50% solution) | 12 |
| Sodium stannate | 0.04 |
| Phosphoric acid | qs pH 2.2 |
| Tetrasodium pyrophosphate | 0.03 |
| Liquid petroleum jelly | 20 |
| Dimethyldiallylammonium chloride homopolymer sold by the company Nalco under the name Merquat 100 | 0.5 |
| Glycerol | 0.5 |
| Cetylstearyl alcohol (30/70 $C_{16}/C_{18}$ - Nafol 1618F) | 8 |
| Oxyethylenated (33 OE) cetylstearyl alcohol | 3 |
| Oxyethylenated (4 OE) rapeseed acid amide | 1.2 |
| Vitamin E: DL-α-tocopherol | 0.1 |
| Water | qs 100 |

Application Mode:

The compositions detailed above are mixed together at the time of use in the following proportions:

10 g of composition C 4 g of composition A or B 16 g of composition D.

The resulting mixtures are then applied to locks of natural hair containing 90% white hairs, at a rate of 10 g of mixture per 1 g of hair.

The mixtures are left on at room temperature for 30 minutes.

The hair is then rinsed, washed with a standard shampoo and dried.

Locks dyed more uniformly and more strongly using the mixture derived from composition A are obtained.

42
Example 2

Dye composition and oxidizing composition of the agent of the invention:

| Dye composition | Weight % |
|---|---|
| Liquid petroleum jelly | 50 |
| Octyldodecanol | 9 |
| Distearyldimethylammonium-modified hectorite | 1.3 |
| Propylene carbonate | 0.45 |
| Oleyl alcohol 10 OE | 5 |
| Propylene glycol | 2 |
| Ethanol | 3 |
| Hexylene glycol | 1 |
| Dipropylene glycol | 1 |
| Monoethanolamine | 4 |
| POE/POP/POE (Poloxamer 184) | 13 |
| Ascorbic acid | 0.25 |
| para-Phenylenediamine | 0.03 |
| Resorcinol | 0.04 |
| 1-Hydroxy-3-aminobenzene | 0.002 |
| 1-β-Hydroxyethyloxy-2,4-diaminobenzene dihydrochloride | 0.0003 |
| N,N-Bis(2-hydroxyethyl)-p-phenylenediamine sulfate monohydrate | 0.006 |
| Water | qs 100 |

This composition is stable over time.

| Oxidizing composition | Weight % |
|---|---|
| Pentasodium pentetate | 0.15 |
| Hydrogen peroxide (aqueous 50% solution) | 12 |
| Sodium stannate | 0.04 |
| Phosphoric acid | qs pH 2.2 |
| Tetrasodium pyrophosphate | 0.03 |
| Liquid petroleum jelly | 20 |
| Dimethyldiallylammonium chloride homopolymer sold by the company Nalco under the name Merquat 100 | 0.5 |
| Glycerol | 0.5 |
| Cetylstearyl alcohol (30/70 $C_{16}/C_{18}$ - Nafol 1618F) | 8 |
| Oxyethylenated (33 OE) cetylstearyl alcohol | 3 |
| Oxyethylenated (4 OE) rapeseed acid amide | 1.2 |
| Vitamin E: DL-α-tocopherol | 0.1 |
| Water | qs 100 |

Application Mode:

The compositions detailed above are mixed together on a weight-for-weight basis at the time of use.

The resulting mixture is then applied to locks of natural hair containing 90% white hairs, at a rate of 10 g of mixture per 1 g of hair.

The mixture is left on the hair at room temperature for 30 minutes.

The hair is then rinsed, washed with a standard shampoo and dried.

Locks dyed in a very light blond shade with an ash-golden tint are obtained.

The invention claimed is:

1. A device or kit for dyeing keratin fibers comprising one or more compartments, wherein:
    (1) a first compartment contains a dye composition free of oxidizing agents, comprising, in a suitable dyeing medium:

at least one hair dye; and at least one polycondensate of ethylene oxide and propylene oxide consisting of polyethylene glycol and polypropylene glycol blocks having the following chemical structure:

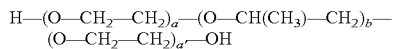

wherein a and a' range from 2 to 150, and b ranges from 1 to 100; and wherein the dye composition is not the following:

| INCI name | g % |
|---|---|
| Beheneth-10 | 6.00 |
| Sorbitol | 5.00 |
| Liquid petroleum jelly | 60.25 |
| Water | 10.00 |
| Ethanol | 2.00 |
| Poloxamer 184 | 5.00 |
| Potassium bicarbonate | 1.75 |
| Water | 4.302 |
| Monoethanolamine | 5.00 |
| p-Phenylenediamine | 0.216 |
| 2,4-Diaminophenoxyethanol dihydrochloride | 0.482 | and (2) an optional second compartment contains an oxidizing composition.

2. A device according to claim 1, wherein the at least one hair dye is chosen from nonionic or ionic synthetic direct dyes, natural dyes and oxidation dye precursors.

3. A device according to claim 1, wherein a and a' range from 10 to 130 and b ranges from 20 to 80.

4. A device according to claim 1, wherein a and a' are identical.

5. A device according to claim 1, wherein the at least one polycondensate of ethylene oxide and propylene oxide has a weight-average molecular weight ranging from 1,000 to 15,000.

6. A process for dyeing keratin fibers, comprising:
applying to the keratin fibers a dye composition comprising, in a suitable dyeing medium:
at least one hair dye; and
at least one polycondensate of ethylene oxide and propylene oxide consisting of polyethylene glycol and polypropylene glycol blocks having the following chemical structure:

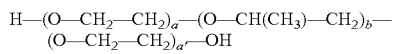

wherein a and a' range from 2 to 150, and b ranges from 1 to 100;

optionally in the presence of at least one oxidizing agent, for a time sufficient to develop the desired coloration;
wherein the dye composition is not chosen from:
(i) the following composition:

| INCI name | g % |
|---|---|
| Beheneth-10 | 6.00 |
| Sorbitol | 5.00 |
| Liquid petroleum jelly | 60.25 |
| Water | 10.00 |
| Ethanol | 2.00 |
| Poloxamer 184 | 5.00 |
| Potassium bicarbonate | 1.75 |
| Water | 4.302 |
| Monoethanolamine | 5.00 |
| p-Phenylenediamine | 0.216 |
| 2,4-Diaminophenoxyethanol dihydrochloride | 0.482 | or (ii) the composition obtained by mixing the emulsion (A1) below:

| Emulsion A1 | | |
|---|---|---|
| Phase | INCI name | g % |
| A | Beheneth-10 | 6.00 |
| | Sorbitol | 5.00 |
| | Liquid petroleum jelly | 60.25 |
| | Water | 10.00 |
| B | Ethanol | 2.00 |
| | Poloxamer 184 | 5.00 |
| | Potassium bicarbonate | 1.75 |
| | Water | 4.302 |
| | Monoethanolamine | 5.00 |
| | p-Phenylenediamine | 0.216 |
| | 2,4-Diaminophenoxyethanol dihydrochloride | 0.482 | with an aqueous composition (B1) comprising a dispersion of fatty alcohols in water (8%) and 6% hydrogen peroxide in a ratio of 1 part by weight of (A1) per 1.5 parts by weight of (B1).

7. A method for increasing the dissolution of at least one hair dye in a dye composition, comprising adding to the dye composition at least one polycondensate of ethylene oxide and propylene oxide consisting of polyethylene glycol and polypropylene glycol blocks having the following chemical structure:

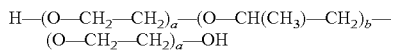

wherein a and a' range from 2 to 150, and b ranges from 1 to 100.

8. An agent for dyeing and/or bleaching keratin fibers, obtained by mixing a composition A comprising at least one alkaline agent with a composition B comprising at least one oxidizing agent,
wherein compositions A and/or B comprise at least one fatty substance free of carboxylic acid groups, at least one polycondensate of ethylene oxide and propylene oxide, and a system comprising at least one nonionic surfactant other than polycondensates of ethylene oxide and propylene oxide, with a weighted HLB of greater than or equal to 8, and
wherein the at least one fatty substance is present in an amount greater than 20% by weight relative to the total weight of the dyeing and/or bleaching agent;
with the exception of an agent obtained by mixing the emulsion (A1) below:

| Emulsion A1 | | |
|---|---|---|
| Phase | INCI name | g % |
| A | Beheneth-10 | 6.00 |
| | Sorbitol | 5.00 |
| | Liquid petroleum jelly | 60.25 |
| | Water | 10.00 |

-continued

Emulsion A1

| Phase | INCI name | g % |
|---|---|---|
| B | Ethanol | 2.00 |
|  | Poloxamer 184 | 5.00 |
|  | Potassium bicarbonate | 1.75 |
|  | Water | 4.302 |
|  | Monoethanolamine | 5.00 |
|  | p-Phenylenediamine | 0.216 |
|  | 2,4-Diaminophenoxyethanol dihydrochloride | 0.482 | with an aqueous composition (B1) comprising a dispersion of fatty alcohols in water (8%) and 6% hydrogen peroxide in a ratio of 1 part by weight of (A1) per 1.5 parts by weight of (B1).

9. An agent according to claim 8, wherein the at least one alkaline agent is chosen from organic amines, mineral bases, salts of organic amines, ammonium salts and aqueous ammonia.

10. An agent according to claim 8, wherein the at least one oxidizing agent is chosen from hydrogen peroxide, urea peroxide, alkali metal bromates or ferricyanides, peroxygenated salts and alkali metal or alkaline-earth metal percarbonates.

11. An agent according to claim 8, wherein the at least one fatty substance is chosen from compounds that are liquid at room temperature and at atmospheric pressure.

12. An agent according to claim 11, wherein the at least one fatty substance is chosen from alkanes comprising from 6 to 16 carbon atoms, fatty alcohols, fatty acid esters, fatty alcohol esters, non-silicone oils of mineral origin containing more than 16 carbon atoms, or non-silicone oils of plant or synthetic origin, silicones, and hydrocarbons containing more than 16 carbon atoms.

13. An agent according to claim 8, wherein the at least one polycondensate of ethylene oxide and propylene oxide is chosen from polyethylene glycol/polypropylene glycol/polyethylene glycol triblock condensates having the following chemical structure:

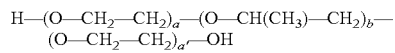

wherein a and a' range from 2 to 150, and b ranges from 1 to 100.

14. An agent according to claim 13, wherein the at least one polycondensate of ethylene oxide and propylene oxide has a weight-average molecular weight ranging from 1,000 to 15,000.

15. An agent according to claim 8, wherein the at least one nonionic surfactant is oxyalkylenated.

16. An agent according to claim 8, wherein the at least one nonionic surfactant has an HLB of greater than or equal to 8.

17. An agent according to claim 8, wherein all the surfactants are nonionic.

18. An agent according to claim 8, wherein the at least one polycondensate of ethylene oxide and propylene oxide and optionally all or some of the nonionic surfactant system with a weighted HLB of greater than 8 and/or all or some of the fatty substances free of carboxylic acid groups are present in composition A.

19. An agent according to claim 8, wherein composition A further comprises at least one oxidation dye and/or at least one direct dye.

* * * * *